US011155553B2

(12) United States Patent
Tripier et al.

(10) Patent No.: US 11,155,553 B2
(45) Date of Patent: Oct. 26, 2021

(54) REINFORCED MACROCYCLIC LIGANDS, COMPLEXES THEREOF, AND USES OF SAME

(71) Applicants: GUERBET, Villepinte (FR); Centre national de la recherche scientifique, Paris (FR); UNIVERSITE DE BRETAGNE OCCIDENTALE, Brest (FR)

(72) Inventors: Raphaël Tripier, Kersaint Plabennec (FR); Olivier Rousseaux, Senlis (FR); Mariane Le Fur, Brest (FR); Maryline Beyler, Brest (FR); Olivier Fougère, Mortefontaine (FR); Gwladys Nizou, Brest (FR)

(73) Assignees: GUERBET, Villepinte (FR); UNIVERSITE DE BRETAGNE OCCIDENTALE, Brest (FR); Centre national de la recherche scientifique, Paris (FR)

(*) Notice: Subject to any disclaimer, the term of this patent is extended or adjusted under 35 U.S.C. 154(b) by 19 days.

(21) Appl. No.: 16/626,645

(22) PCT Filed: Jun. 28, 2018

(86) PCT No.: PCT/EP2018/067482
§ 371 (c)(1),
(2) Date: Dec. 26, 2019

(87) PCT Pub. No.: WO2019/002505
PCT Pub. Date: Jan. 3, 2019

(65) Prior Publication Data
US 2020/0157101 A1 May 21, 2020

(30) Foreign Application Priority Data
Jun. 28, 2017 (FR) ................................. 17 55933

(51) Int. Cl.
C07D 471/18 (2006.01)
A61K 51/04 (2006.01)
A61K 9/00 (2006.01)
A61K 51/12 (2006.01)

(52) U.S. Cl.
CPC .......... *C07D 471/18* (2013.01); *A61K 9/0019* (2013.01); *A61K 51/0482* (2013.01); *A61K 51/121* (2013.01)

(58) Field of Classification Search
CPC .. A61K 2121/00; A61K 2123/00; A61K 9/00; A61K 9/0019; A61K 51/00; A61K 51/04; A61K 51/0482; A61K 51/121; C07D 471/18
USPC .... 424/1.11, 1.65, 1.69, 1.81, 1.85, 9.1, 9.2; 534/7, 10–16; 514/1, 1.1
See application file for complete search history.

(56) References Cited

U.S. PATENT DOCUMENTS

| 10,711,001 B2* | 7/2020 | Le Fur ................... A61P 35/00 |
| 2019/0023705 A1 | 1/2019 | Le Fur et al. |
| 2021/0017180 A1* | 1/2021 | Hamon .............. A61K 49/0019 |

FOREIGN PATENT DOCUMENTS

WO 2017/109217 A1 6/2017

OTHER PUBLICATIONS

Le Fur et al, Inorg. Chem., Feb. 5, 2018, Vo. 57, pp. 2051-2063 (Year: 2018).*
Le Fur et al, Chem. Commun., Aug. 3, 2017, vol. 53, pp. 9534-9537 (Year: 2017).*
Dioury et al., "Synthesis of a Tricyclic Tetraazatriacetic Ligand for Gadolinium(III) as Potential Contrast Agent for MRI", Tetrahedron, Oct. 2006, pp. 204-214, vol. 63.
Hancock et al., "More Rigid Macrocyclic Ligands That Show Metal Ion Size-Based Selectivity. A Crystallographic, Molecular Mechanics, and Formation Constant Study of the Complexes of Bridged Cyclen", Journal of the American Chemical Society, 1988, vol. 110, pp. 2788-2794.
Ramasubbu et al., "Structurally Reinforced Cyclen: A Rigidly trans-Co-ordinating Twelve-membered Macrocycle", Journal of the Chemical Society, Chemical Communications, 1982, pp. 277-278.

* cited by examiner

*Primary Examiner* — D. L. Jones
(74) *Attorney, Agent, or Firm* — Thompson Coburn LLP; Steven M. Ritchey

(57) ABSTRACT

Ligands that are based on the pyclen macrocycle that are reinforced, which are useful for complexing elements such as radioelements and/or elements with magnetic properties.

17 Claims, 5 Drawing Sheets

REINFORCED MACROCYCLIC LIGANDS, COMPLEXES THEREOF, AND USES OF SAME

CROSS-REFERENCE TO RELATED APPLICATIONS

This application is a U.S. National Phase application of PCT/EP2018/067482 filed on Jun. 28, 2018, claiming the benefit of French Application No. 17 55933, filed on Jun. 28, 2017, both of which are incorporated herein by reference in their entireties.

The present invention relates to novel reinforced macrocyclic ligands and also to complexes thereof, in particular radioactive complexes thereof, and to the respective uses thereof.

The present invention also relates to a process for preparing said ligands and complexes.

Macrocyclic ligands and the corresponding metal complexes thereof are used in many fields, such as medical imaging, therapy or else chemical catalysis. These ligands make it possible to complex metals by virtue of their structure forming a cavity so as to trap and complex the metal.

In order to limit the flexibility of these ligands and/or to functionalize their structure, an additional carbon bridge is added to the basic macrocyde: the ligands thus formed are called reinforced ligands. This addition makes it possible to have access to highly preorganized macrocycles having a three-dimensional internal cavity, the nature of which depends on the size of the macrocycle and also on the length of the bridge.

Applied to tetraazamacrocycles, the additional carbon bridge can be located on adjacent nitrogen atoms (side-bridged) or opposite nitrogen atoms (cross-bridged).

To date, only three types of bridged tetraazamacrocycles exist:
- the "ansa macrocycles", which are macrobicycles, the additional carbon bridge of which comprises at least four atoms;
- the "azacages", which are spherical macrotricycles that have two carbon bridges located on the pairs of opposite nitrogen atoms;
- reinforced tetraazamacrocycles, which are macrobicycles that have an ethylene or propylene bridge. Among the reinforced structures, only macrocycles of cyclene or cyclam type are known.

There is thus a need for new reinforced ligands, allowing in particular the formation of thermodynamically stable and kinetically inert metal complexes. In particular, there is a need for new reinforced ligands based on a pyclen macrocycle and allowing the formation of stable, in particular thermodynamically stable, and kinetically inert metal complexes.

The objective of the present invention is to provide new ligands which are based on the pyclen macrocycle and are reinforced, and which make it possible to complex chemical elements, in particular radioelements and/or elements with magnetic properties.

An objective of the present invention is also to provide new complexes of these ligands, in particular radioactive and/or magnetically active complexes An objective of the present invention is to provide ligands and/or complexes that are particularly useful in medical imaging and/or in therapy for example as contrast agents.

An objective of the present invention is also to provide a pharmaceutical composition comprising complexes with reinforced ligands.

An objective of the present invention is to provide ligands and/or complexes that are useful as chemical catalysts.

An objective of the present invention is to provide a process for preparing these ligands and complexes.

The present invention relates to a compound of general formula (I) below:

(I)

[Structure of formula (I) showing a pyridine-containing macrocycle with substituents $X_1$, $X_2$, $X_3$ on the pyridine ring, $Y_1$, $Y_2$, $Y_3$, $Y_4$, $Y_5$, $Y_6$ on the ring carbons, $Z_1$, $Z_2$ on the bridging carbons, and an N—R group]

wherein:
$X_1$, $X_2$, $X_3$, $Y_1$, $Y_2$, $Y_3$, $Y_4$, $Y_5$ and $Y_6$ are chosen, independently of one another, from the group consisting of:

H, $(C_1\text{-}C_{20})$alkyl, $(C_2\text{-}C_{20})$alkenyl, $(C_2\text{-}C_{20})$alkynyl, $(C_6\text{-}C_{10})$aryl, halogen, azide (—$N_3$), —C(O)ORa, —ORa, —N(Ra)(Rb), —C(O)—N(Ra)(Rb), —SH, —SRa, —$SO_2OH$, —$SO_2$—N(Ra)(Rb), —SCN and a functional chemical group which allows grafting to a vector or to a biomolecule; Ra and Rb being, independently of one another, H or a $(C_1\text{-}C_{20})$alkyl group;

it being possible for said alkyl, alkenyl and alkynyl groups to optionally comprise one or more heteroatom(s) and/or one or more $(C_6\text{-}C_{10})$arylene(s) and/or one or more biphenylene(s) in their chain; and it being possible for said alkyl, alkenyl, alkynyl and $(C_6\text{-}C_{10})$aryl groups to optionally be substituted with one or more substituent(s) chosen from the group consisting of: halogen, —C(O)ORc, —ORc, —N(Rc)(Rd), —C(O)—N(Rc)(Rd), —SH, —SRc, —$SO_2OH$, —$SO_2$—N(Rc)(Rd)-SCN, $(C_6\text{-}C_{10})$aryl and a functional chemical group which allows grafting to a vector or a biomolecule;

Rc and Rd being, independently of one another, H or a $(C_1\text{-}C_{20})$alkyl group; it being possible for said alkyl group to be optionally substituted with one or more substituent(s) chosen from the group consisting of: halogen, —C(O)ORe, —ORe, —N(Re)(Rf), —C(O)—N(Re)(Rf), —SH, —SRe, —$SO_2OH$, —$SO_2$—N(Re)(Rf)—SCN, $(C_6\text{-}C_{10})$aryl and a functional chemical group which allows grafting to a vector or a biomolecule;

Re and Rf being, independently of one another, H or a $(C_1\text{-}C_{20})$alkyl group;

$Z_1$ and $Z_2$ are chosen, independently of one another, from the group consisting of:

H, $(C_1\text{-}C_4)$alkyl, halogen, —ORg, —N(Rg)(Rh), —SH and —SRg,

Rg and Rh being, independently of one another, chosen from the group consisting of:

H, a $(C_1\text{-}C_4)$alkyl, 2-THP (tetrahydropyranyl), tosyl, nosyl or TMS (trimethylsilyl) group, —O—C(O)Rt, —C(O)Rt, —OC(O)ORt, —NH—C(O)—ORt, —NH—C(O)Rt; Rt being chosen from: $(C_1-C_4)$alkyl such as methyl or tert-butyl, benzyl, allyl or trifluoromethyl;

it being possible for said alkyl groups to be optionally substituted with one or more substituent(s) chosen from the group consisting of:

halogen, —C(O)ORp, —ORp, —N(Rp)(Rq), —C(O)—N(Rp)(Rq), —SH, —SRp, —SO$_2$OH, —SO$_2$—N(Rp)(Rq) and —SCN; Rp and Rq being, independently of one another, H or a $(C_1-C_4)$alkyl group;

R is chosen from the group consisting of:

H, $(C_1-C_{20})$alkyl, $(C_2-C_{20})$alkenyl, $(C_2-C_{20})$alkynyl, $(C_1-C_{20})$alkylene-W, $(C_2-C_{20})$alkenylene-W and $(C_2-C_{20})$alkynylene-W;

it being possible for said alkyl, alkenyl, alkynyl, alkylene, alkenylene and alkynylene groups to optionally comprise one or more heteroatom(s) and/or one or more $(C_6-C_{10})$arylene(s) and/or one or more biphenylene(s) in their chain;

W being chosen from the group consisting of:

$(C_6-C_{10})$aryl, heteroaryl consisting of 5 to 10 atoms, biphenyl, —C(O)ORi, —C(O)—N(Ri)(Rj), —P(O)(ORi)(ORj), —(Rj)P(O)(ORi), —O—P(O)(ORi)(ORj), —SH, —SO$_2$OH, —SO$_2$—N(Ri)(Rj) and —SCN;

Ri and Rj being, independently of one another, H or a $(C_1-C_{20})$alkyl group;

it being possible for said alkyl, alkenyl, alkynyl, alkylene, alkenylene, alkynylene, aryl and heteroaryl groups to optionally be substituted with one or more substituent(s) chosen from the group consisting of:

$(C_1-C_{20})$alkyl, $(C_2-C_{20})$alkenyl, $(C_2-C_{20})$alkynyl, halogen, —C(O)ORk, —ORk, —N(Rk)(Rl), —C(O)—N(Rk)(Rl), —SH, —SRk, —SO$_2$OH, —SO$_2$N(Rk)(Rl), —SCN, $(C_6-C_{10})$aryl and biphenyl;

Rk and Rl being, independently of one another, H or a $(C_1-C_{20})$alkyl group, it being possible for said alkyl to be optionally substituted with one or more substituent(s) chosen from the group consisting of:

halogen, —C(O)ORm, —ORm, —N(Rm)(Rn), —C(O)—N(Rm)(Rn), —SH, —SRm, —SO$_2$OH, —SO$_2$—N(Rm)(Rn), —SCN, $(C_6-C_{10})$aryl and a functional chemical group which allows grafting to a vector or a biomolecule;

Rm and Rn being, independently of one another, H or a $(C_1-C_{20})$alkyl group;

or a pharmaceutically acceptable salt thereof or an optical isomer thereof or a geometric isomer thereof or a tautomer thereof or a solvate thereof.

The inventors have developed new ligand-metal complexes (complexes also known as chelates) from the pyclen macrocycle (3,6,9,15-tetraazabicyclo[9.3.1]pentadeca-1(15),11,13-triene). The pyclen macrocycle has the following formula and thus differs from cyclene or cyclam macrocycles:

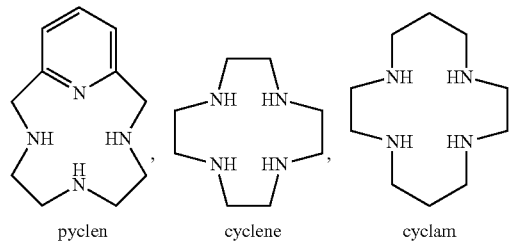

pyclen  cyclene  cyclam

The reinforced structure of the ligands according to the invention is the following, based on a substituted pyclen macrocyde and comprising an ethylene bridge between two nitrogen atoms which are adjacent and not involved in the aromatic ring:

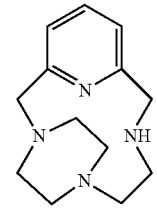 [SMILES: c1cc2nc(c1)CN1CCN(CCNC2)CC1]

The inventors have discovered that the ethylene bridge induces a structural constraint on the pyclen ring due to the bridged nitrogen atoms coming closer together.

Thus, the size of the internal cavity of the ligand is smaller and much more rigid than that of nonreinforced pyclens. The doublets of the nitrogen atoms point in restricted directions and involve pre-organization of the ligand.

This structural modification makes it possible in particular to complex the metals stably and the complexes are thus inert. It is therefore possible to prepare complexes that are more thermodynamically stable but also more kinetically inert.

These properties are important when the compounds are used in particular in vivo, since this reduces the risk of undesired release of the complexed element in the event of competition with the medium (other metal or nonmetal cations), other chelating entities, or detrimental conditions (reducing medium for example). Furthermore, the steric constraints and the reduced size of the cavity allow improved selectivity with respect to certain metals.

In particular, the new reinforced ligands and their complexes can be vectorized by means of the grafting of biomolecules or of vectors, thereby making it possible to target therapeutic use thereof or use thereof in medical imaging.

Definitions

The term "ligand" is intended to mean a compound capable of complexing a chemical element such as a metal, preferably a radioelement. According to one embodiment, for the purposes of the invention, the ligands are in anionic form and can complex chemical elements in cationic form. According to the present invention, the compounds of formula (I) are ligands, more particularly reinforced ligands.

According to one embodiment, the term "reinforced ligand" is intended to mean a pyclen macrocyde comprising an additional ethylene bridge connecting two adjacent nitrogen atoms of said macrocyde.

The term "radioelement" is intended to mean any known radioisotope of a chemical element, whether it is natural or artificially produced.

The term "element with magnetic properties" is intended to mean in particular any element which, subjected to a magnetic induction, begins to produce itself, in the volume that it occupies and outside, a magnetic induction, and also any paramagnetic element which, not having a spontaneous magnetization property, acquires, under the effect of an outside magnetic field, a magnetization directed in the same direction as this excitation field.

The term "complex" is intended to mean the association of a ligand as defined above with a chemical element such as a metal, preferably a radioelement as defined above and/or an element with magnetic properties as defined above. The term "complex" is synonymous with "chelate".

In the context of the invention, the term "treating", "treatment" or "therapeutic treatment" means reversing, relieving, inhibiting the progression of the disorder or of the ailment to which this term is applicable, or one or more symptoms of such a disorder, preferably a pathological disorder.

The term "medical imaging" denotes the means of acquiring and restoring images of the human or animal body using various physical phenomena such as X-ray absorption, nuclear magnetic resonance, ultrasonic wave reflection or radioactivity. According to one embodiment, the term "medical imaging" refers to X-ray imaging, MRI (magnetic resonance imaging), Single Photon Emission Computed Tomography (SPECT), positron emission tomography (PET) and luminescence. Preferably, the medical imaging method is X-ray imaging. According to one particular embodiment, the medical imaging method is MRI if the complex according to the invention comprises Gd(III), SPECT if the complex according to the invention comprises a gamma emitter and PET if the complex according to the invention comprises a beta+ emitter.

The term "($C_1$-$C_{20}$)alkyl" denotes saturated aliphatic hydrocarbons, which may be linear or branched and comprise from 1 to 20 carbon atoms. Preferably, the alkyls comprise from 1 to 10 carbon atoms, more preferentially from 1 to 5 carbon atoms. The term "branched" is intended to mean that an alkyl group is substituted on the main alkyl chain. The preferred alkyls according to the invention are methyl, ethyl, propyl, isopropyl or tert-butyl.

The term "($C_1$-$C_{20}$)alkylene" denotes an alkyl radical as defined above and which is divalent. The preferred alkylenes according to the invention are ($C_1$-$C_3$)alkylenes, that is to say methylene, ethylene and propylene and more preferentially methylene.

The term "($C_2$-$C_{20}$)alkenyl" denotes an alkyl as defined above, comprising at least one carbon-carbon double bond.

The term "($C_2$-$C_{20}$)alkenylene" denotes an akyl as defined above, comprising at least one carbon-carbon double bond and which is divalent.

The term "($C_2$-$C_{20}$)alkynyl" denotes an alkyl as defined above, comprising at least one carbon-carbon triple bond.

The term "($C_2$-$C_{20}$)alkynylene" denotes an alkyl as defined above, comprising at least one carbon-carbon triple bond and which is divalent.

The term "($C_6$-$C_{10}$)aryl" denotes monocyclic, bicyclic or tricyclic, hydrocarbon-based aromatic compounds, in particular phenyl and naphthyl.

According to one embodiment, the biphenyl radicals may be substituted in a manner identical to the aryls according to the invention.

The term "heteroaryl consisting of 5 to 10 atoms" denotes monocyclic, bicyclic or tricyclic, hydrocarbon-based aromatic compounds comprising from 5 to 10 carbon atoms and in which at least one of the carbon atoms is replaced with a heteroatom, preferably N. According to one embodiment, the heteroaryl is a pyridinyl, thiazolyl or indazolyl group.

The term "($C_6$-$C_{10}$)arylene" denotes an aryl as defined above and which is divalent, in particular phenylene and naphthylene.

According to one embodiment, the term "halogen" denotes F, Cl, Br, I, At and the isotopes thereof, preferably F, Cl, Br, I and the isotopes thereof. According to one embodiment, the term "halogen" denotes F, Cl, Br, I, At, preferably F, Cl, Br and I.

Among the heteroatoms, mention may in particular be made of P, N, O and S, preferably N and O. According to one particular embodiment, the akyl, alkenyl and akynyl groups of the compounds of general formula (I) comprise 1 or 2 heteroatom(s).

The term "vector" is intended to mean in particular nanovectors, active ingredients, liposomes, micelles, microparticles, nanoparticles, particles based on iron oxide (Ultra Small Particle of Iron Oxide (USPIO), Small Particle of Iron Oxide (SPIO)), polymersomes and molecule aggregates.

The term "biomolecule" is intended to mean in particular peptides such as cyclic peptides, pseudopeptides, polypeptides, proteins or functional domains of proteins, haptens, antibodies, antibody fragments, vitamins, hormones, nucleosides, nucleotides, DNA, RNA or DNA or RNA fragments, fatty acids or fatty acid derivatives, phospholipids or phospholipid derivatives, cholesterol or cholesterol derivatives, monosaccharides, oligosaccharides, polysaccharides and polyamines.

The expression "functional chemical group which allows grafting to a vector or to a biomolecule" is intended to mean any chemical group or chemical function which allows, after reaction, the coupling of a ligand according to the invention with a vector or a biomolecule as defined above.

According to one embodiment, the expression "functional chemical group which allows grafting to a vector or a biomolecule" is intended to mean a group chosen from the group consisting of: succinimidyl, N-hydroxysuccinimidyl, sulfosuccinimidyl, maleimidyl, biotinyl, squarate, true alkynylene (that is to say an alkynylene of formula

with R1 being an alkylene), thiol (—SH), azide (—$N_3$), hydrazine (—NH—$NH_2$) and isothiocyanate (—SCN).

The term "Lipiodol" refers to an iodinated oil and preferentially to the pharmaceutical specialty product Lipiodol®, an injectable solution manufactured and sold by the company Guerbet consisting of ethyl esters, of iodinated poppyseed oil fatty acids. Lipiodol is a product in particular used for visualization, localization and/or vectorization during transarterial chemoembolization of intermediate-stage hepatocellular carcinoma in adults, and also for the diagnosis, via the selective hepatic arterial route, of the hepatic extension of hepatic or nonhepatic malignant lesions.

Compounds of General Formula (I)

The compounds of general formula (I), or reinforced ligands according to the invention, can have centers of chirality and can be in various isomeric forms. The invention thus also relates to the optical isomers (enantiomers or racemic mixture), geometric isomers (diastereoisomers, cis/trans or Z/E isomers), tautomers and solvates such as hydrates of the compounds of general formula (I).

According to one embodiment, the compounds of general formula (I) are in salt form, preferably in the form of a pharmaceutically acceptable salt.

The term "pharmaceutically acceptable salt" denotes in particular nontoxic salts which make it possible to retain the properties of the compounds according to the invention. Examples of pharmaceutically acceptable salts are found in Berge et al. ((1977) J. Pharm. Sd, vol. 66, 1). The term "pharmaceutically acceptable salts" is intended to mean in particular organic or mineral acid or base salts. For example, the compounds of general formula (I) are the form of a hydrochloride, hydrobromide, sodium or meglumine salt.

Preferably, in formula (I) below, $X_1$, $X_2$, $X_3$, $Y_1$, $Y_2$, $Y_3$, $Y_4$, $Y_5$ and $Y_6$ are chosen, independently of one another, from the group consisting of:

H, $(C_1-C_{20})$alkyl, $(C_2-C_{20})$alkenyl, $(C_2-C_{20})$alkynyl, $(C_6-C_{10})$aryl, halogen, azide (—$N_3$), —C(O)ORa, —ORa, —N(Ra)(Rb), —C(O)—N(Ra)(Rb), —SH, —$SO_2$OH, —SCN and a functional chemical group which allows grafting to a vector or to a biomolecule; Ra and Rb being, independently of one another, H or a $(C_1-C_{20})$ alkyl group;

it being possible for said alkyl, alkenyl and alkynyl groups to optionally comprise one or more heteroatom(s) and/or one or more $(C_6-C_{10})$arylene(s) and/or one or more biphenylene(s) in their chain; and it being possible for said alkyl, alkenyl, alkynyl and $(C_6-C_{10})$aryl groups to optionally be substituted with one or more substituent(s) chosen from the group consisting of: halogen. —C(O)ORc, —ORc, —N(Rc)(Rd), —C(O)—N(Rc)(Rd), —SH, —$SO_2$OH. —SCN, $(C_6-C_{10})$aryl and a functional chemical group which allows grafting to a vector or a biomolecule:

Rc and Rd being, independently of one another, H or a $(C_1-C_{20})$alkyl group;

it being possible for said alkyl group to be optionally substituted with one or more substituent(s) chosen from the group consisting of:

halogen, —C(O)ORe, —ORe, —N(Re)(Rf), —C(O)—N(Re)(Rf), —SH, —$SO_2$OH, —SCN, $(C_6-C_{10})$aryl and a functional chemical group which allows grafting to a vector or a biomolecule;

Re and Rf being, independently of one another, H or a $(C_1-C_{20})$alkyl group;

$Z_1$ and $Z_2$ are chosen, independently of one another, from the group consisting of:

H, $(C_1-C_4)$alkyl, halogen, —ORg, —N(Rg)(Rh), and —SH,

Rg and Rh being, independently of one another, chosen from the group consisting of:

H, a $(C_1-C_4)$alkyl, 2-THP (tetrahydropyranyl), tosyl, nosyl or TMS (trimethylsilyl) group, —O—C(O)Rt, —C(O)Rt, —OC(O)Rt, —NH—C(O)—ORt, —NH—C(O)Rt;

Rt being chosen from: $(C_1-C_4)$alkyl such as methyl or tert-butyl, benzyl, allyl or trifluoromethyl;

it being possible for said alkyl groups to be optionally substituted with one or more substituent(s) chosen from the group consisting of:

halogen, —C(O)ORp, —ORp, —N(Rp)(Rq), —C(O)—N(Rp)(Rq), —SH, —$SO_2$OH, and —SCN; Rp and Rq being, independently of one another, H or a $(C_1-C_4)$ alkyl group;

R is chosen from the group consisting of:

H, $(C_1-C_{20})$alkyl, $(C_2-C_{20})$alkenyl, $(C_2-C_{20})$alkynyl, $(C_1-C_{20})$alkylene-W, $(C_2-C_{20})$alkenylene-W and $(C_2-C_{20})$ alkynylene-W;

it being possible for said alkyl, alkenyl, alkynyl, alkylene, alkenylene and alkynylene groups to optionally comprise one or more heteroatom(s) and/or one or more $(C_6-C_{10})$arylene(s) and/or one or more biphenylene(s) in their chain;

W being chosen from the group consisting of:

$(C_6-C_{10})$aryl, heteroaryl consisting of 5 to 10 carbon atoms, biphenyl, —C(O)ORi, —C(O)—N(Ri)(Rj), —P(O)(ORi)(ORj), —P(O)(ORi), —O—P(O)(ORi)(ORj), —SH, —$SO_2$H and —SCN;

Ri and Rj being, independently of one another, H or a $(C_1-C_{20})$alkyl group;

it being possible for said alkyl, alkenyl, alkynyl, alkylene, alkenylene, alkynylene, aryl and heteroaryl groups to be optionally substituted with one or more substituent(s) chosen from the group consisting of:

$(C_1-C_{20})$alkyl, $(C_2-C_{20})$alkenyl, $(C_2-C_{20})$alkynyl, halogen, —C(O)ORk, —ORk, —N(Rk)(Rl), —C(O)—N(Rk)(Rl), —SH, —$SO_2$H, —SCN, $(C_6-C_{10})$aryl and biphenyl;

Rk and Rl being, independently of one another, H or a $(C_1-C_{20})$alkyl group, it being possible for said alkyl to be optionally substituted with one or more substituent(s) chosen from the group consisting of:

halogen, —C(O)ORm, —ORm, —N(Rm)(Rn), —C(O)—N(Rm)(Rn), —SH, —$SO_2$OH, —SCN, $(C_6-C_{10})$aryl and a functional chemical group allowing grafting to a vector or a biomolecule;

Rm and Rn being, independently of one another, H or a $(C_1-C_{20})$alkyl group.

According to one embodiment, R is chosen from the group consisting of: H, $(C_1-C_{20})$alkyl, $(C_1-C_{20})$alkylene-W; it being possible for said alkyl and alkylene groups to optionally comprise one or more heteroatom(s) and/or one or more $(C_6-C_{10})$arylene(s) and/or one or more biphenylene(s) in their chain, preferably a biphenylene group;

W being chosen from the group consisting of:

$(C_6-C_{10})$aryl, heteroaryl consisting of 5 to 10 atoms, —C(O)ORi, —C(O)—N(Ri)(Rj), —P(O)(ORi)(ORj), —(Rj)P(O)(ORi), —O—P(O)(ORi)(ORj), —SH, —SRi, —$SO_2$OH, —$SO_2$—N(Ri)(Rj), —SCN and a biphenyl group;

Ri and Rj being, independently of one another, H or a $(C_1-C_{20})$alkyl group;

it being possible for said alkyl, alkylene, aryl and heteroaryl groups to be optionally substituted with one or more substituent(s) chosen from the group consisting of:

$(C_1-C_{20})$alkyl, $(C_2-C_{20})$alkenyl, $(C_2-C_{20})$alkynyl, halogen, —C(O)ORk, —ORk, —N(Rk)(Rl), —C(O)—N(Rk)(Rl), —SH, —SRk, —$SO_2$OH, —$SO_2$—N(Rk)(Rl), —SCN, $(C_6-C_{10})$aryl and a biphenyl group;

Rk and Rl being, independently of one another, H or a $(C_1-C_{20})$alkyl group.

According to one particular embodiment, R is chosen from the group consisting of:

H, $(C_1-C_{20})$alkyl, $(C_1-C_{20})$alkylene-W;

W being a phenyl or pyridinyl group, it being possible for said alkyl, alkylene, phenyl or pyridinyl groups to be optionally substituted with one or more substituent(s) chosen from the group consisting of:

$(C_1-C_{20})$alkyl, $(C_2-C_{20})$alkenyl, $(C_2-C_{20})$alkynyl, halogen, —C(O)ORk, —ORk, —N(Rk)(Rl), —C(O)—N(Rk)(Rl), —SH, —SRk, —$SO_2$OH, —$SO_2$—N(Rk)(Rl)-SCN, $(C_6-C_{10})$aryl and a biphenyl group;

Rk and Rl being, independently of one another, H or a (C$_1$-C$_{20}$)alkyl group.

According to one embodiment, R is chosen from the group consisting of:

H, (C$_1$-C$_{20}$)alkyl, (C$_1$-C$_{20}$)alkylene-W;

W being chosen from the group consisting of:

(C$_6$-C$_{10}$)aryl, heteroaryl consisting of 5 to 10 atoms, —C(O)ORi, —C(O)—N(Ri)Rj), —P(O)(ORi)(ORj), —(Rj)P(O)(ORi), —O—P(O)(ORi)(ORj), —SH, —SO$_2$OH, —SO$_2$—N(Ri)(Rj) and —SCN;

Ri and Rj being, independently of one another, H or a (C$_1$-C$_{20}$)alkyl group;

it being possible for said alkyl, alkylene, aryl and heteroaryl groups to be optionally substituted with one or more substituent(s) chosen from the group consisting of:

(C$_1$-C$_{20}$)alkyl, (C$_2$-C$_{20}$)alkenyl, (C$_2$-C$_{20}$)alkynyl, halogen, —C(O)ORk, —ORk, —N(Rk)(Rl), —C(O)—N(Rk)(Rl), —SH, —SRk, —SO$_2$OH, —SO$_2$—N(Rk)(Rl), —SCN and (C$_6$-C$_{10}$)aryl;

Rk and Rl being, independently of one another, H or a (C$_1$-C$_{20}$)alkyl group.

According to one particular embodiment, R is chosen from the group consisting of:

H, (C$_1$-C$_{20}$)alkyl, (C$_1$-C$_{20}$)alkylene-W;

W being chosen from the group consisting of:

(C$_6$-C$_{10}$)aryl, heteroaryl consisting of 5 to 10 atoms, —C(O)ORi, —C(O)—N(Ri)Rj), —P(O)(ORi)(ORj), —P(O)(ORi), —O—P(O)(ORi)(ORj), —SH, —SO$_2$OH and —SCN;

Ri and Rj being, independently of one another, H or a (C$_1$-C$_{20}$)alkyl group;

it being possible for said alkyl, alkylene, aryl and heteroaryl groups to be optionally substituted with one or more substituent(s) chosen from the group consisting of: (C$_1$-C$_{20}$)alkyl, (C$_2$-C$_{20}$)alkenyl, (C$_2$-C$_{20}$)alkynyl, halogen, —C(O)ORk, —ORk, —N(Rk)(Rl), —C(O)—N(Rk)(Rl), —SH, —SO$_2$OH, —SCN and (C$_6$-C$_{10}$)aryl;

Rk and Rl being, independently of one another, H or a (C$_1$-C$_{20}$)alkyl group.

According to one particular embodiment, R is chosen from H, (C$_1$-C$_5$)alkylene-C(O)ORk or is of formula (i) below:

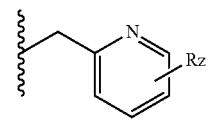

(i)

Rz being chosen from (C$_1$-C$_{10}$)alkyl, (C$_2$-C$_{10}$)alkenyl, (C$_2$-C$_{10}$)alkynyl, halogen, —C(O)ORk, —ORk, —N(Rk)(Rl), —C(O)—N(Rk)(Rl), —SH, —SRk, —SO$_2$OH, —SO$_2$N(Rk)(Rl) and —SCN;

Rk and Rl being, independently of one another, H or a (C$_1$-C$_{10}$)alkyl group.

According to one embodiment, R is chosen from H, (C$_1$-C$_{20}$)alkyl, (C$_2$-C$_{20}$)alkenyl, (C$_2$-C$_{20}$)alkynyl, (C$_1$-C$_{20}$)alkylene-W, (C$_1$-C$_{20}$)alkenylene-W and (C$_1$-C$_{20}$)alkynylene-W;

W being chosen from the group consisting of:

—COOH, —P(O)(OH)$_2$, —(Rl)P(O)—OH, —OH, —SH, —C(O)—N(Ri)(Rj) with Ri and Rj as defined above, and

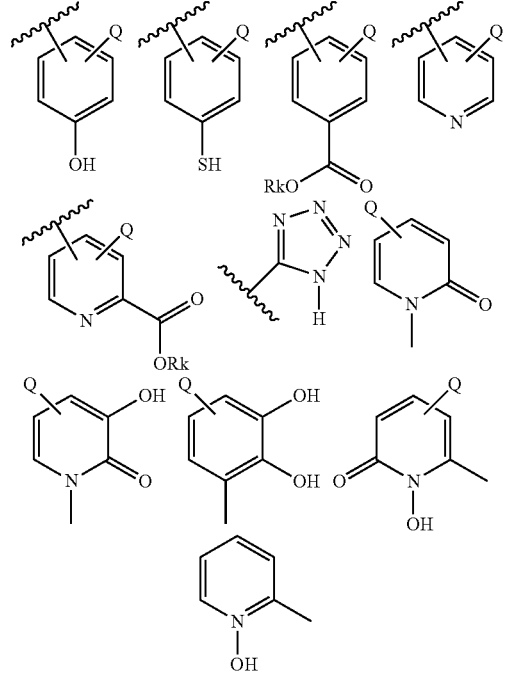

Q being chosen from (C$_1$-C$_{20}$)alkyl, (C$_2$-C$_{20}$)alkenyl, (C$_2$-C$_{20}$)alkynyl, halogen, —C(O)ORk, —ORk, —N(Rk)(Rl), —C(O)—N(Rk)(Rl), —SH, —SRk, —SO$_2$OH, —SO$_2$—N(Rk)(Rl) and —SCN;

Rk and Rl being, independently of one another, H or a (C$_1$-C$_{20}$)alkyl group.

According to one embodiment, R is chosen from H, (C$_1$-C$_{20}$)alkyl, (C$_2$-C$_{20}$)alkenyl, (C$_2$-C$_{20}$)alkynyl, (C$_1$-C$_{20}$)alkylene-W, (C$_1$-C$_{20}$)alkenylene-W and (C$_1$-C$_{20}$)alkynylene-W;

W being chosen from the group consisting of:

—COOH, —P(O)(OH)$_2$, —P(O)—OH, —OH, —SH, —C(O)—N(Ri)(Rj) with Ri and Rj as defined above, and

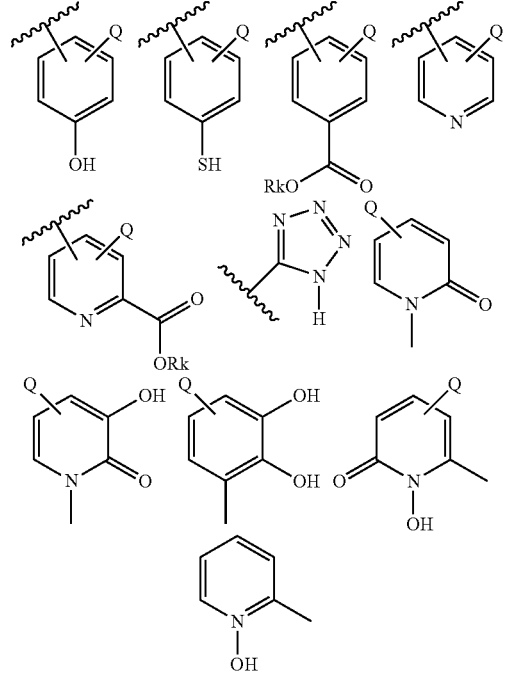

Q being chosen from (C$_1$-C$_{20}$)alkyl, (C$_2$-C$_{20}$)alkenyl, (C$_2$-C$_{20}$)alkynyl, halogen, —C(O)ORk, —ORk, —N(Rk)(Rl), —C(O)—N(Rk)(Rl), —SH, —SO$_2$OH and —SCN;

Rk and Rl being, independently of one another, H or a (C$_1$-C$_{20}$)alkyl group.

According to one embodiment, R is chosen from H, (C$_1$-C$_5$)alkyl, (C$_1$-C$_5$)alkylene-W; W being chosen from the group consisting of:

—COOH, —P(O)(OH)$_2$, -(Q)P(O)OH,

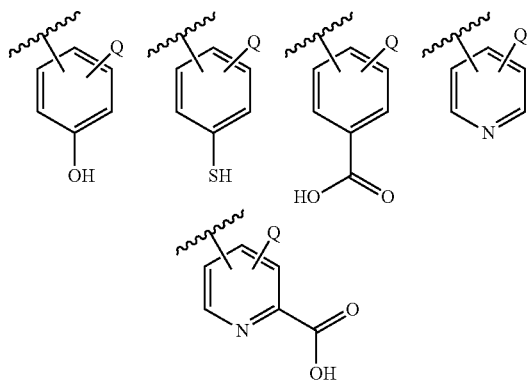

with Q being as defined above,
and preferably W being chosen from the group consisting of:
—COOH, —P(O)(OH)$_2$, —P(O)—OH,

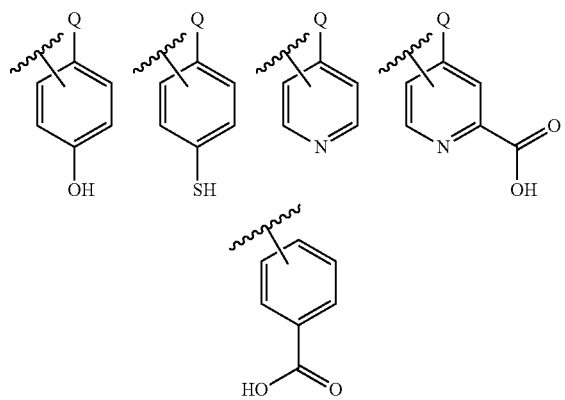

with Q being as defined above.

According to one embodiment, R is different than H.

According to one embodiment, W is chosen from a (C$_6$-C$_{10}$)aryl, a heteroaryl consisting of 5 to 10 atoms, or a —C(O)ORi group with Ri as defined above.

According to one particular embodiment, W is a phenyl, a pyridinyl or a —C(O)ORi group with Ri as defined above.

According to one particular embodiment, Z$_1$ and Z$_2$, which may be identical or different, are H, OH or Cl, preferably H. According to one embodiment, X$_1$, X$_2$, X$_3$, Y$_1$, Y$_2$, Y$_3$, Y$_4$, Y$_5$ and Y$_6$ are chosen, independently of one another, from the group consisting of:
H, (C$_1$-C$_{20}$)alkyl, (C$_2$-C$_{20}$)alkenyl, (C$_2$-C$_{20}$)alkynyl, halogen, azide (—N$_3$).
it being possible for said alkyl, alkenyl and alkynyl groups to optionally comprise one or more heteroatom(s) and/or one or more (C$_6$-C$_{10}$)arylene(s) and/or one or more biphenylene(s) in their chain; and
it being possible for said alkyl, alkenyl and alkynyl groups to be optionally substituted with one or more substituent(s) chosen from the group consisting of:
halogen, —C(O)ORc, —ORc, —N(Rc)(Rd), —C(O)—N(Rc)(Rd), —SH, —SRc, —SO$_2$OH, —SO$_2$—N(Rc)(Rd)-SCN, (C$_6$-C$_{10}$)aryl and a functional chemical group which allows grafting to a vector or a biomolecule
(preferably from the group consisting of halogen, —C(O)ORc, —ORc, —N(Rc)(Rd), —C(O)—N(Rc)(Rd), —SH, —SO$_2$OH, —SO$_2$—N(Rc)(Rd)-SCN, (C$_6$-C$_{10}$)aryl and a functional chemical group which allows grafting to a vector or a biomolecule);

Rc and Rd being, independently of one another, H or a (C$_1$-C$_{20}$)alkyl group.

According to one embodiment, X$_1$, X$_2$ and X$_3$ are chosen, independently of one another, from the group consisting of: H, halogen, (C$_2$-C$_{20}$)alkynyl, (C$_6$-C$_{10}$)aryl or azide, more preferentially H.

According to one embodiment, Y$_1$, Y$_2$, Y$_3$, Y$_4$, Y$_5$ and Y$_6$ are chosen, independently of one another, from the group consisting of:
H, (C$_1$-C$_{20}$)alkyl, (C$_2$-C$_{20}$)alkenyl and (C$_2$-C$_{20}$)alkynyl, it being possible for said alkyl, alkenyl and alkynyl groups to optionally comprise one or more heteroatom(s) and/or one or more (C$_6$-C$_{10}$)arylene(s) and/or one or more biphenylene(s) in their chain.

According to one particular embodiment, Y$_1$, Y$_2$, Y$_3$, Y$_4$, Y$_5$ and Y$_6$ are H.

According to one particular embodiment Y$_2$ and Y$_3$ are H or OH, preferably H.

According to one embodiment, the compounds according to the invention have formula (II) below:

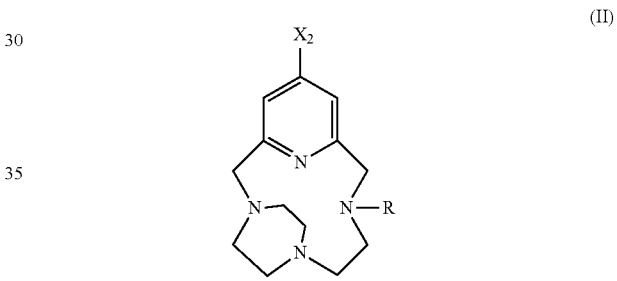

with X$_2$ and R being as defined above, preferably X$_2$ is H, halogen, (C$_2$-C$_{20}$)alkynyl, (C$_6$-C$_{10}$)aryl or azide, more preferentially H.

The invention also relates to a compound chosen from the group consisting of the following compounds:

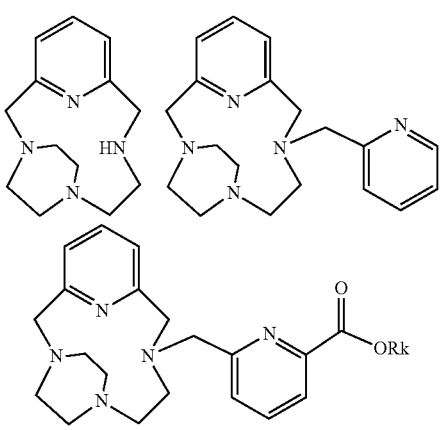

wherein Rk is H or a (C$_1$-C$_{20}$)alkyl group, in particular H or a (C$_1$-C$_4$)alkyl group, preferably a methyl,

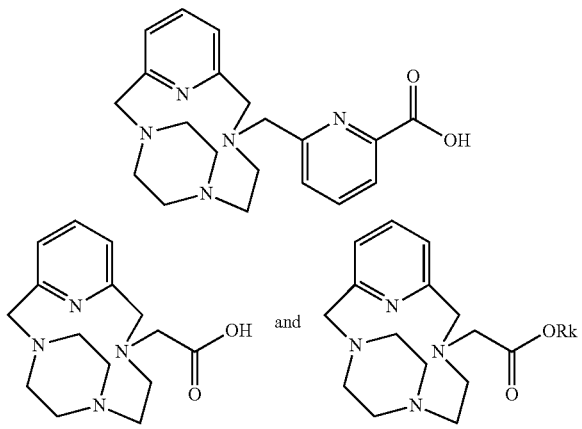

wherein Rk is H or a $(C_1-C_{20})$alkyl group, in particular H or a $(C_1-C_4)$alkyl group, preferably a t-butyl.

According to one embodiment, the alkyl groups of the Ra, Rb, Rc and Rd radicals are not substituted. According to one embodiment, the alkyl groups of the $Z_1$ and $Z_2$ radicals are not substituted.

According to one embodiment, the compounds according to the invention have general formula (I) below:

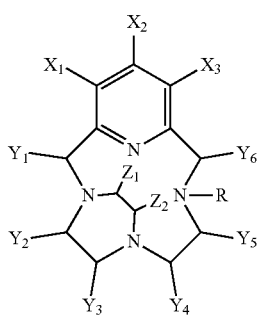

wherein:
$X_1$, $X_2$, $X_3$, $Y_1$, $Y_2$, $Y_3$, $Y_4$, $Y_5$ and $Y_6$ are chosen, independently of one another, from the group consisting of:
H, $(C_1-C_{20})$alkyl, $(C_2-C_{20})$alkenyl, $(C_2-C_{20})$alkynyl, $(C_6-C_{10})$aryl, halogen,
—C(O)ORa, —ORa, —N(Ra)(Rb), —C(O)—N(Ra)(Rb), —SH, —SRa, —SO$_2$OH, SO$_2$—N(Ra)(Rb), —SCN and a functional chemical group which allows grafting to a vector or to a biomolecule; Ra and Rb being, independently of one another, H or a $(C_1-C_{20})$ alkyl group;
it being possible for said alkyl, alkenyl and alkynyl groups to optionally comprise one or more heteroatom(s) and/or one or more $(C_6-C_{10})$arylene(s) and/or one or more biphenylene(s) in their chain;
$Z_1$ and $Z_2$ are chosen, independently of one another, from the group consisting of:
H, $(C_1-C_4)$alkyl, halogen, —ORg, —N(Rg)(Rh), —SH and —SRg;
Rg and Rh being, independently of one another, H or a $(C_1-C_4)$alkyl group;
R is chosen from the group consisting of:
H, $(C_1-C_{20})$alkyl, $(C_2-C_{20})$alkenyl, $(C_2-C_{20})$alkynyl, $(C_1-C_{20})$alkylene-W, $(C_2-C_{20})$alkenylene-W and $(C_2-C_{20})$alkynylene-W;

W being chosen from the group consisting of:
$(C_6-C_{10})$aryl, heteroaryl consisting of 5 to 10 atoms, —C(O)ORi, —C(O)—N(Rl)(Rj), —P(O)(ORi)(ORj), —(Rj)P(O)(ORi), —O—P(O)(ORi)(ORj), —SH, —SO$_2$OH, —SO$_2$—N(Ri)(Rj), and —SCN;
Ri and RJ being, independently of one another, H or a $(C_1-C_{20})$alkyl group;
it being possible for said alkyl, alkenyl, alkynyl, alkylene, alkenylene, alkynylene, aryl and heteroaryl groups to be optionally substituted with one or more substituent(s) chosen from the group consisting of:
$(C_1-C_{20})$alkyl, $(C_2-C_{20})$alkenyl, $(C_2-C_{20})$alkynyl, halogen, —C(O)ORk, —ORk, —N(Rk)(Rl), —C(O)—N(Rk)(Rl), —SH, —SRk, —SO$_2$OH, —SO$_z$—N(Rk)(Rl), —SCN and $(C_6-C_{10})$aryl;
Rk and Rl being, independently of one another, H or a $(C_1-C_{20})$alkyl group.

Complexes

The invention also relates to a complex of a compound of formula (I) or of a salt thereof, as defined above, with a chemical element M, preferably a metal. According to one embodiment, M is a metal cation. According to one embodiment, M is a natural metal cation or a radioelement, preferentially a radioelement.

According to one embodiment, M is chosen from transition metals (Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, Db, Sg, Bh, Hs, Cn), rare earth metals (Sc, Y, La, Ce, Pr, Nd, Pm, Sm, Eu, Gd, Tb, Dy, Ho, Er, Tm, Yb and Lu), strontium (Sr), magnesium (Mg), rubidium (Rb), gallium (Ga), zinc (Zn), arsenic (As), aluminum (Al), lead (Pb), bismuth (Bi) and indium (In).

According to one embodiment, M is chosen from transition metals (Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, Db, Sg, Bh, Hs, Cn), strontium (Sr), magnesium (Mg), rubidium (Rb), gallium (Ga), zinc (Zn), arsenic (As), aluminum (Al), lead (Pb), bismuth (Bi) and indium (In).

According to one particular embodiment, M is chosen from transition metals (Sc, Ti, V, Cr, Mn, Fe, Co, Ni, Cu, Y, Zr, Nb, Mo, Tc, Ru, Rh, Pd, Ag, Hf, Ta, W, Re, Os, Ir, Pt, Au, Rf, Db, Sg, Bh, Hs, Cn).

According to one particular embodiment, M is chosen from lanthanides and is preferentially Gd, and in particular the $Gd^{3+}$ ion.

According to one particular embodiment, M is chosen from Mn, Fe, Co, Ni, Cu, Zn, Ga, As, Sc, Al, Tc, Pd and Pt. M is even more preferentially chosen from Mn, Fe, Co, Ni, Cu, Zn and Ga.

The stable or radioactive forms of these elements may be: $^{68}Ga$, $^{67}Ga$, $^{52}Mn$, $^{52m}Mn$, $^{99m}Tc$, $^{99}Tc$, $^{91}Y$, $^{91m}Y$, $^{90}Y$, $^{88}Y$, $^{55}Fe$, $^{59}Fe$, $^{195m}Pt$, $^{103}Pd$, $^{186}Re$, $^{188}Re$, $^{67}Cu$, $^{64}Cu$, $^{212}Pb$, $^{212}Bi$, $^{213}Bi$, $^{111}In$, $^{26}Al$, $^{82}Sr$, $^{28}Mg$, $^{44}Ti$, $^{47}Sc$, $^{51}Cr$, $^{57}Co$, $^{81}Rb$, $^{82}Rb$, $^{192}Ir$, $^{117m}Sn$.

According to one particular embodiment, in the context of applications in imaging or in therapy as defined below, M is chosen from:
$^{88}Ga$, $^{67}Ga$, $^{52}Mn$, $^{99m}Tc$, $^{90}Y$, $^{86}Y$, $^{59}Fe$, $^{195m}Pt$, $^{103}Pd$, $^{186}Re$, $^{188}Re$, $^{67}Cu$, $^{64}Cu$, $^{212}Pb$, $^{212}Bi$, $^{213}Bi$ and $^{111}In$.

According to another embodiment. In the context of applications in industry as catalysts, M is chosen from: Pd, Rh, Ru, Pt, Ag, Au and Re.

According to another embodiment, in the context of applications in in vitro diagnostic tools, M is chosen from the lanthanides, Fe, Rh and Ru.

Pharmaceutical Composition

The invention also relates to a pharmaceutical composition comprising a compound of formula (I) as defined above or a complex as defined above, and optionally one or more pharmaceutically acceptable excipient(s).

The composition may also comprise a buffer chosen from commonly used buffers such as, for example, lactate, tartrate, malate, maleate, succinate, ascorbate, carbonate, tris ((hydroxymethyl)aminomethane), HEPES (2-[4-(2-hydroxyethyl)-1-piperazine]ethanesulfonic acid) and MES (2-morpholinoethanesulfonic acid) buffers, phosphate buffered saline (often abbreviated to PBS) and mixtures thereof.

The pharmaceutical composition may comprise an oily phase, in particular an iodinated oil. According to one particular embodiment, the pharmaceutical composition also comprises ethyl esters of iodinated poppyseed oil fatty acids.

According to one embodiment, the pharmaceutical composition according to the invention consists of an iodinated oil and of complexes according to the invention. Typically, the pharmaceutical composition according to the invention consists of Lipiodol) and of complexes according to the invention. Lipiodol® consists of ethyl esters of iodinated poppyseed oil fatty acids.

Preferably, the pharmaceutical composition according to the invention is radioopaque, and thus visible by X-ray radiography.

According to one particular embodiment, the pharmaceutical composition is an injectable composition. According to one embodiment, the pharmaceutical composition according to the invention is administered by intra-arterial hepatic injection.

The present invention also relates to a method for imaging the whole body or a part of the body of an individual, comprising a step of obtaining one or more images of the whole body or of a pert of the body of an individual by means of a medical imaging technique, wherein said whole body or said part of the body of the individual comprises the complex or the pharmaceutical composition as defined above.

The invention also relates to a contrast product comprising the complex of a compound of formula (I) or of a salt thereof as defined above.

The invention also relates to a complex or a pharmaceutical composition as defined above, for use in medical imaging.

The invention also relates to the use of a complex or of a pharmaceutical composition as defined above in medical imaging.

According to one embodiment, it will be possible to use the following imaging techniques depending on the nature of the chemical element M of the complex as defined above:

in the case where the chemical element M is a gamma-ray emitter, Single Photon Emission Computed Tomography (SPECT) can be used, in the case where the chemical element M is a position emitter, Positron Emission Tomography (PET), also called PET scan can be used, in the case where the chemical element M is gadolinium or manganese, magnetic resonance imaging (MRI) can be used.

The invention relates to a complex of a compound of formula (I) or of a salt thereof as defined above, for use for in vivo diagnosis purposes.

The Invention also relates to the use of a complex according to the invention as a catalyst, in particular in stereospecific, stereoselective, diastereospecific, and diastereoselective stereospecific reactions and coupling reactions.

The invention relates to a complex or pharmaceutical composition as defined above, for use in cancer treatment.

The invention relates to the use of a complex as defined above, for preparing a medicament for cancer treatment.

The invention relates to a method of therapeutic treatment of a patient suffering from a cancer, comprising the administration to said patent of a complex or of a pharmaceutical composition as defined above. In particular, said treatment method does not comprise a surgical treatment step.

The therapeutic treatment method, the complex or the pharmaceutical composition for use in cancer treatment, as defined above, is based in particular on the fact that the chemical element M of the complex or of a pharmaceutical composition as defined above emits radiation which destroys the cancer cells. The complex as defined above, used for preparing a medicament for cancer treatment, comprises in particular a chemical element M which emits beta (minus) radiation, Auger electrons or alpha particles.

The term "cancer" is intended to mean an abnormal cell proliferation (also known as tumor) within a normal tissue of the organism. These cancer cells all derive from one and the same clone, a cancer initiating cell, which has acquired certain characteristics that allow it to divide indefinitely. During the progression of the tumor, some cancer cells can migrate out of their site of production and form metastases.

Among cancers, mention may in particular be made of liver cancers, in particular primary liver cancers, preferably hepatocarcinomas. According to one particular embodiment, among cancers, mention may be made of hepatocarcinoma, epithelioid hemangloendothelioma, cholangiocarcinoma, neuroendocrine tumors and metastases of other cancers, such as colorectal cancer metastases.

According to one particular embodiment, the cancer is an intermediate-stage hepatocellular carcinoma in adults.

Process for Preparing the Compounds of General Formula (I) and Complexation

The invention relates to a process for preparing a compound of general formula (I) below:

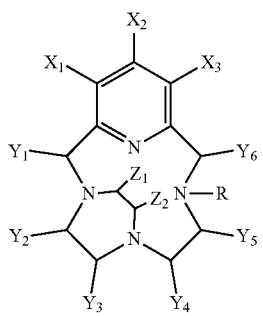

(I)

$X_1, X_2, X_3, Y_1, Y_2, Y_3, Y_4, Y_5, Y_6, Z_1, Z_2$ and R being as defined above, said process comprising a step C of reducing a compound of formula (XIII) below:

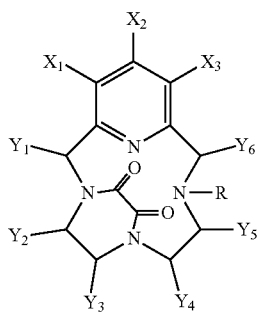

(XIII)

wherein $X_1$, $X_2$, $X_3$, $Y_1$, $Y_2$, $Y_3$, $Y_4$, $Y_5$, $Y_6$ and R are as defined above, in the presence of a mixture of a reducing agent $A\text{-}BH_4$ and of an organic acid, with A being chosen from the group consisting of Li, Na, K, Zn and $(Me_3)N$;

in order to obtain a compound of formula (I') below:

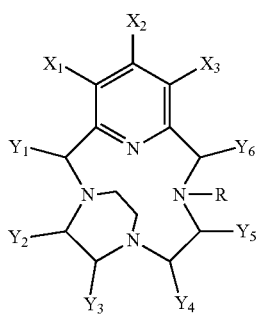

(I')

wherein $X_1$, $X_2$, $X_3$, $Y_1$, $Y_2$, $Y_3$, $Y_4$, $Y_5$, $Y_6$ and R are as defined above.

The compounds of formula (I') correspond to compounds of formula (I) wherein $Z_1=Z_2=H$.

Generally, the reducing step C results in the formation of an intermediate compound of formula (XX):

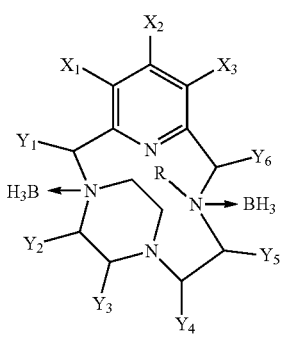

(XX)

wherein $X_1$, $X_2$, $X_3$, $Y_1$, $Y_2$, $Y_3$, $Y_4$, $Y_5$, $Y_6$ and R are as defined above.

In one embodiment, the reducing step C results in the formation of at least one of the intermediate compounds of formulae (XXI) and (XXII) below:

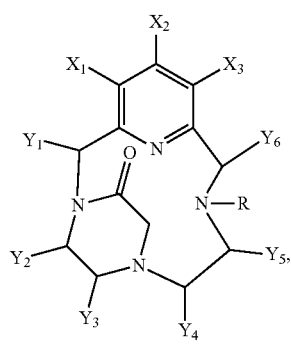

(XXI)

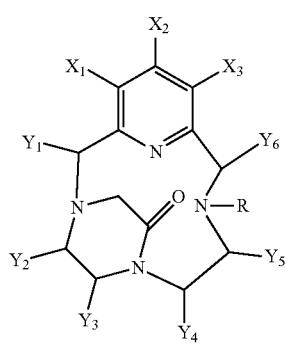

(XXII)

wherein $X_1$, $X_2$, $X_3$, $Y_1$, $Y_2$, $Y_3$, $Y_4$, $Y_5$, $Y_6$ and R are as defined above.

According to one preferred embodiment, the reducing step C is carried out in the presence of a mixture of the reducing agent $NaBH_4$ with trifluoroacetic acid ($NaBH_4$/TFA mixture).

According to one embodiment, the organic acid is chosen from acetic acid, trifluoroacetic acid, and mixtures thereof. According to one embodiment, the acetic acid is used as a mixture with $NaBH_4$ or $(Me)_4NBH_4$. According to another embodiment, the trifluoroacetic acid is used as a mixture with $NaBH_4$.

The organic acids and the borohydrides ($A\text{-}BH_4$) that can be used according to the invention are in particular described in Encyclopedia of Reagents for Organic Synthesis (ed. Leo A. Paquette) John Wiley 1995.

According to one embodiment, the $A\text{-}BH_4$/organic acid ratio, preferably the $NaBH_4$/TFA ratio, is 1/1. According to one embodiment, the number of equivalents of the $A\text{-}BH_4$/organic acid mixture is between 2 and 10, preferably 5, per amide function of the compounds of formula (XIII) (that is to say per amide function borne by the nitrogen atoms belonging to the pyclen ring).

According to one embodiment, the reducing step C is carried out in the presence of an organic solvent, preferably chosen from tetrahydrofuran, dichloromethane (also referred to as DCM or $CH_2Cl_2$ below), acetonitrile, methanol, ethanol, chloroform, or mixtures thereof.

According to one embodiment, the reducing step C is carried out under an inert atmosphere. According to one embodiment, the reducing step C is carried out at ambient temperature, that is to say preferably between 15'C and 25° C. According to one embodiment, the mixing of the reducing agent $A\text{-}BH_4$ and of the organic acid is carried out at a temperature between 0° C. and 25° C., preferably approximately 0° C.

According to one embodiment, the process according to the invention comprises, before said reducing step C, a step A of condensing a compound of formula (X) below:

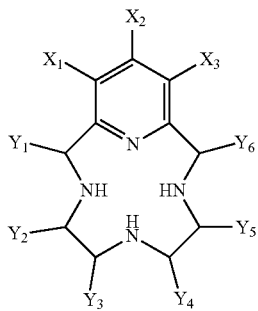

(X)

$X_1$, $X_2$, $X_3$, $Y_1$, $Y_2$, $Y_3$, $Y_4$, $Y_5$ and $Y_6$ being as defined above, with a compound of formula (XI) below:

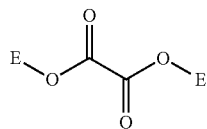

(XI)

with E being a $(C_1-C_4)$alkyl, preferably an ethyl or a methyl.

According to one embodiment, the compound of formula (XI) is chosen from the compounds below:

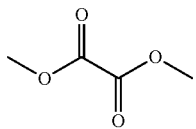

(XI-1)

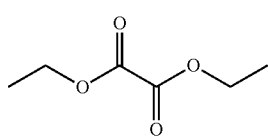

(XI-2)

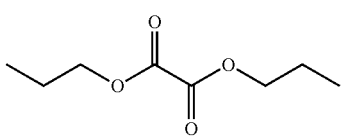

(XI-3)

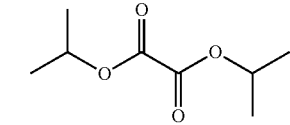

(XI-4)

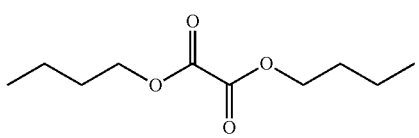

(XI-5)

in order to obtain a compound of formula (XII) below:

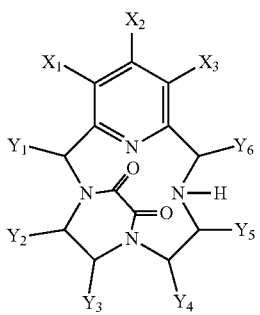

(XII)

$X_1$, $X_2$, $X_3$, $Y_1$, $Y_2$, $Y_3$, $Y_4$, $Y_5$ and $Y_6$ being as defined above.

According to one embodiment, the condensing step A is carried out in the presence of a polar solvent such as methanol, ethanol, or mixtures thereof. According to one embodiment, the condensing step A is carried out at ambient temperature, that is to say between 15° C. and 25° C.

According to one embodiment and when R is different than H, the process for preparing a compound of formula (I) according to the invention comprises, between step A and step C, a step B of functionalizing a compound of formula (XII) below:

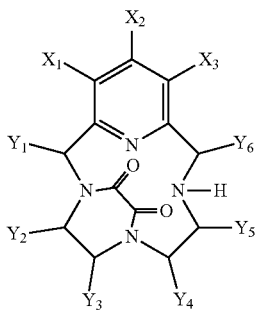

(XII)

$X_1$, $X_2$, $X_3$, $Y_1$, $Y_2$, $Y_3$, $Y_4$, $Y_5$ and $Y_6$ being as defined above, in order to obtain a compound of formula (XIII) below:

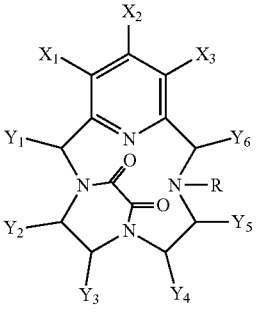

(XIII)

$X_1$, $X_2$, $X_3$, $Y_1$, $Y_2$, $Y_3$, $Y_4$, $Y_5$, $Y_6$ and R being as defined above. "Functionalization B" is intended to mean the addition of the group R, when it is different than H, on a compound of formula (XII).

According to one embodiment, the process for preparing a compound of formula (I) according to the invention comprises, after step C and when at least one of the groups $Z_1$ and $Z_2$ is different than H, a step D' of functionalizing a compound of formula (I') below:

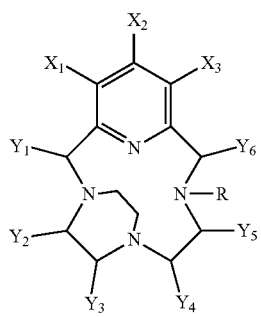

(I')

wherein $X_1$, $X_2$, $X_3$, $Y_1$, $Y_2$, $Y_3$, $Y_4$, $Y_5$, $Y_6$ and R are as defined above,
in order to obtain a compound of formula (I) as according to the invention, wherein at least one of the groups $Z_1$ and $Z_2$ is different than H.

According to one embodiment, the process for preparing a compound of formula (I) according to the invention comprises, before step C and when at least one of the groups $Z_1$ and $Z_2$ is different than H, a step D of functionalizing a compound of formula (XIII) below:

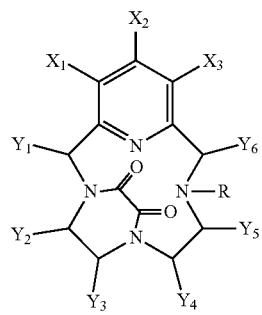

XIII wherein $X_1$, $X_2$, $X_3$, $Y_1$, $Y_2$, $Y_3$, $Y_4$, $Y_5$, $Y_6$ and R are as defined above,
in order to obtain a compound of formula (I) as according to the invention, wherein at least one of the groups $Z_1$ and $Z_2$ is different than H.

"Functionalization D or D'" Is intended to mean the addition or the modification of a group $Z_1$ and/or $Z_2$, in order to obtain, at the end of the process, a compound of formula (I) wherein at least one of the groups $Z_1$ and $Z_2$ is different than H.

The functionalizing steps B and D can be carried out according to methods known to those skilled in the art.

According to one embodiment, steps A, B, C and D as defined above can be linked together in a sequence according to one of the following schemes:

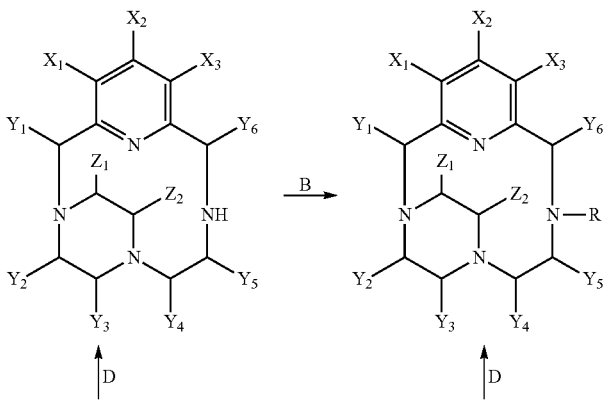

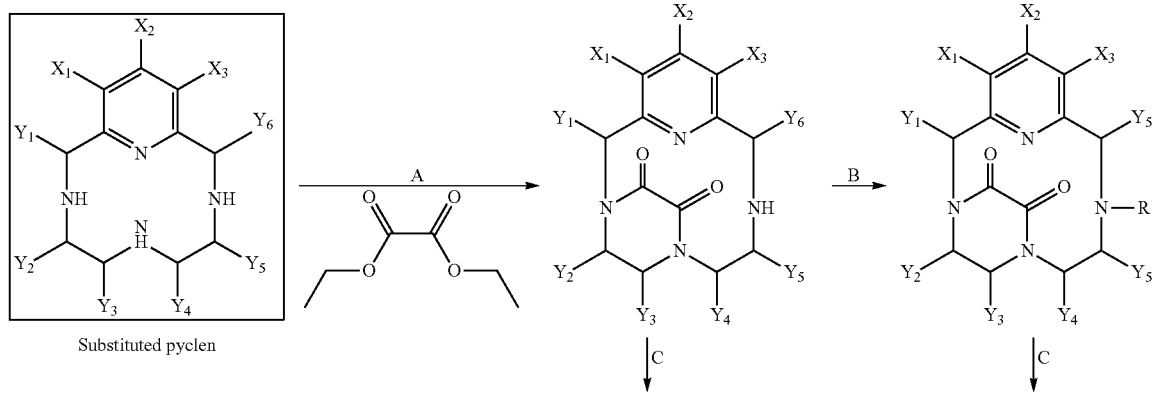

-continued
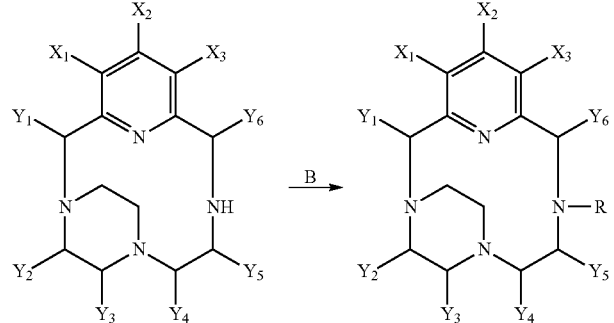
Possible sequence of steps A, B, C, D
A = Condensation
B = Functionalization
C = Reduction
D = Conversion Z
Z other than H
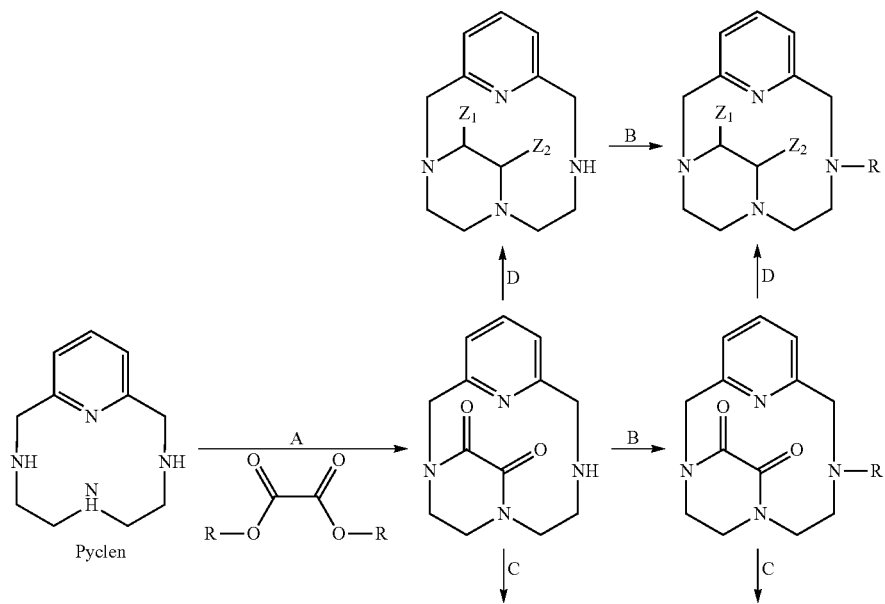
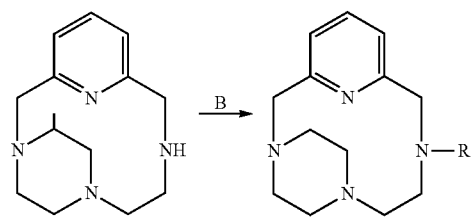
Possible sequence of steps A, B, C, D
A = Condensation
B = Functionalization
C = Reduction
D = Conversion Z
Z other than H According to one embodiment, the reducing C of the compound of the formula below:

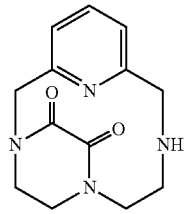 [SMILES: O=C1C(=O)N2CCN1CCNCc1cccc(n1)C2]

results in the formation of at least one of the intermediate compounds having the formulae below:

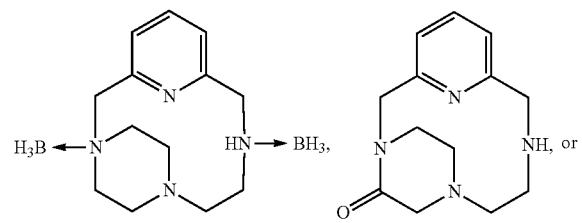

According to one embodiment, the reducing C of the compound of the formula below:

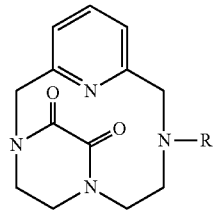

results in the formation of at least one of the intermediate compounds having the formulae below:

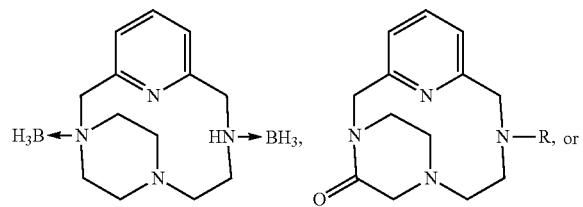

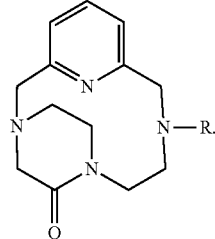

wherein R is as defined above.

According to one embodiment, the functionalizing of the compound having the formula below:

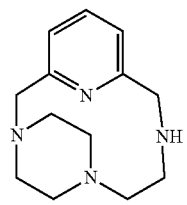

results in the formation of at least one of the intermediate compounds having the formulae below:

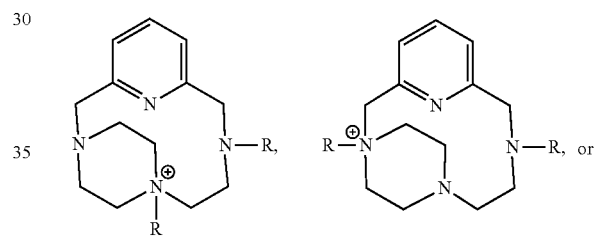

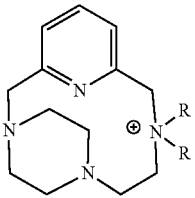

wherein R is as defined above.

According to one embodiment, the process for preparing a compound of formula (I) according to the invention comprises the following steps:
condensing step A as defined above; then
optionally, functionalizing step B as defined above; then
reducing step C as defined above; then
optionally, functionalizing step D as defined above.

The invention also relates to a process for preparing a complex as according to the invention, comprising a step of complexation of a chemical element M as defined above with a ligand according to the invention, said step preferably being a radiolabeling step.

The complexation is preferably carried out by microwaves.

DESCRIPTION OF THE FIGURES

FIG. 1: $^1$H and $^{13}$C NMR spectra of the compound 2a.

FIG. 3: Mass spectrometry of the compound 3a.

Figure 1:
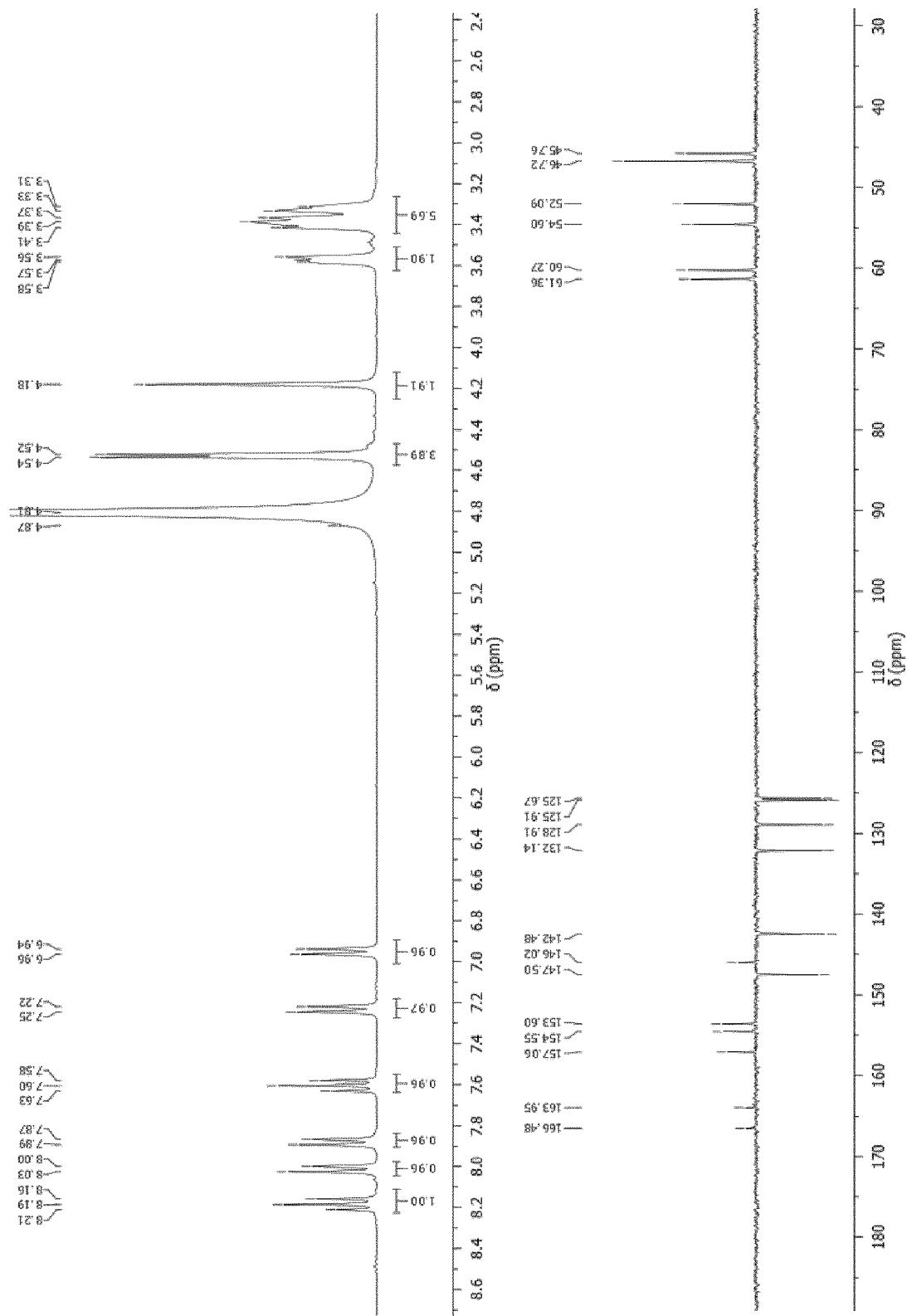
Figure 2:
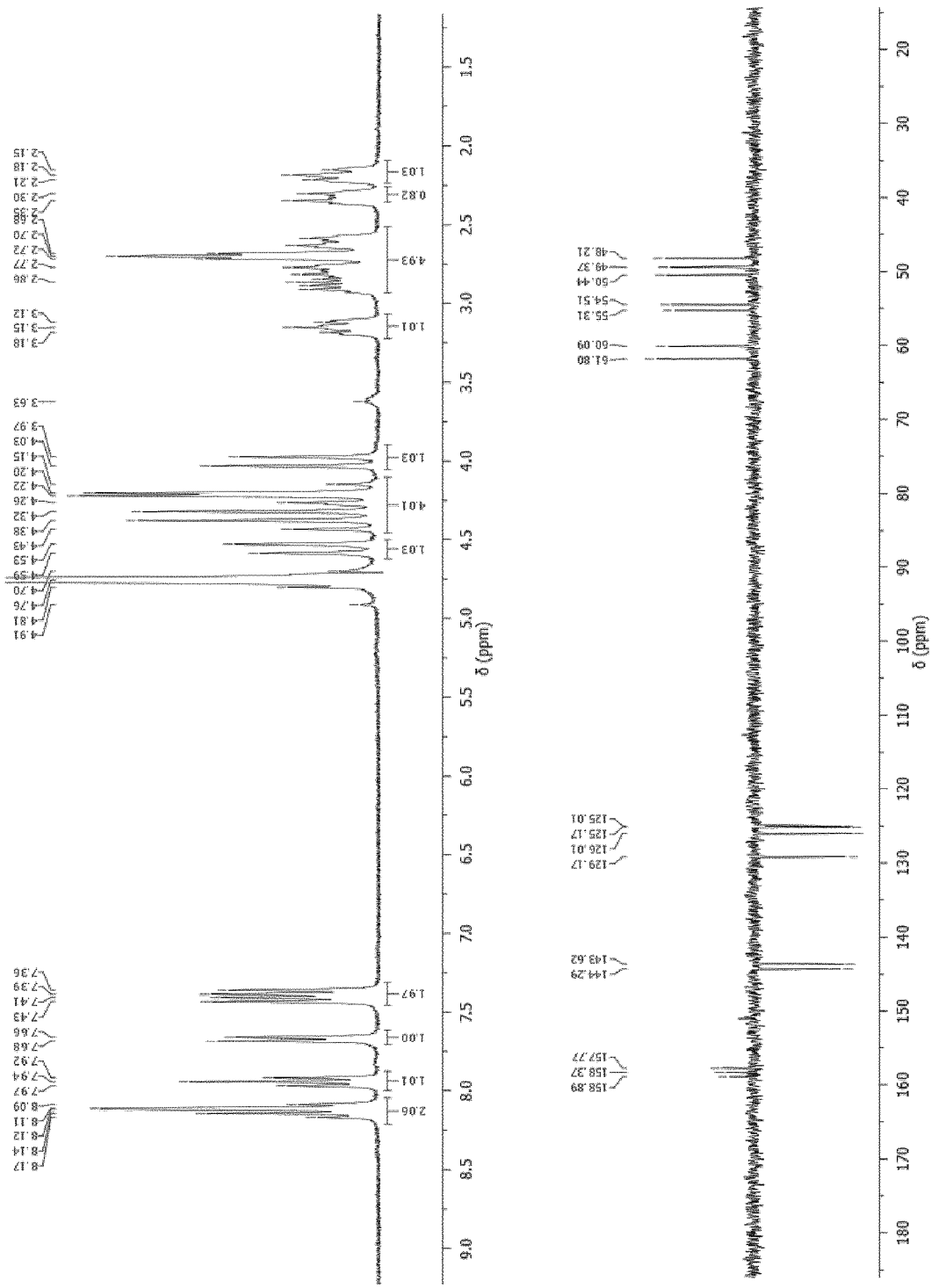
FIG. 2: $^1$H and $^{13}$C NMR spectra of the [Zn(2a)](ClO$_4$) complex.
Figure 4:
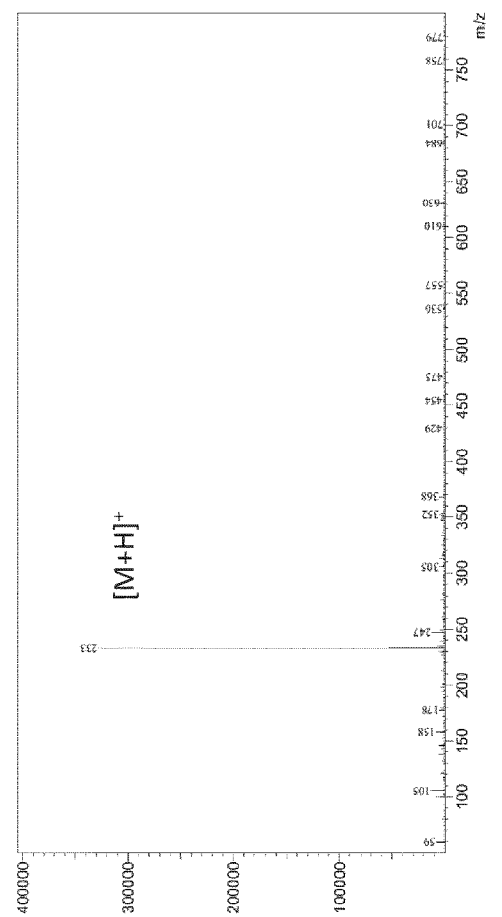
FIG. 4: Mass spectrometry of the compound 4.
Figure 3:
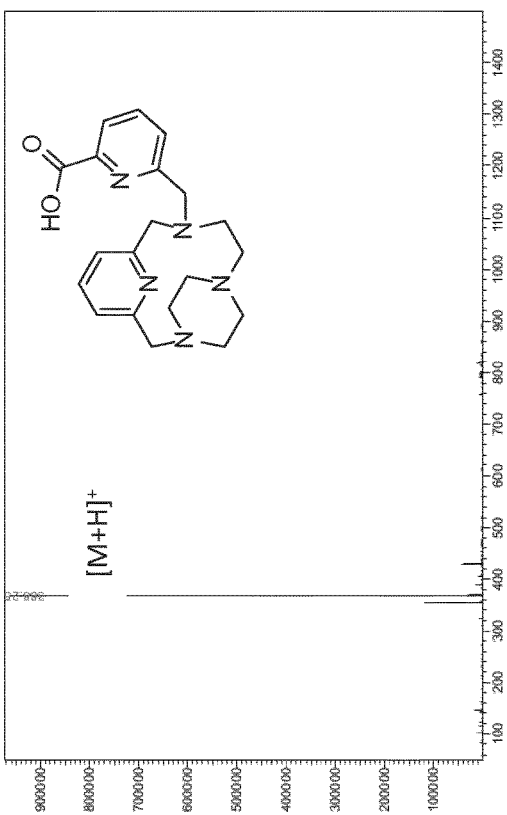
Figure 5:
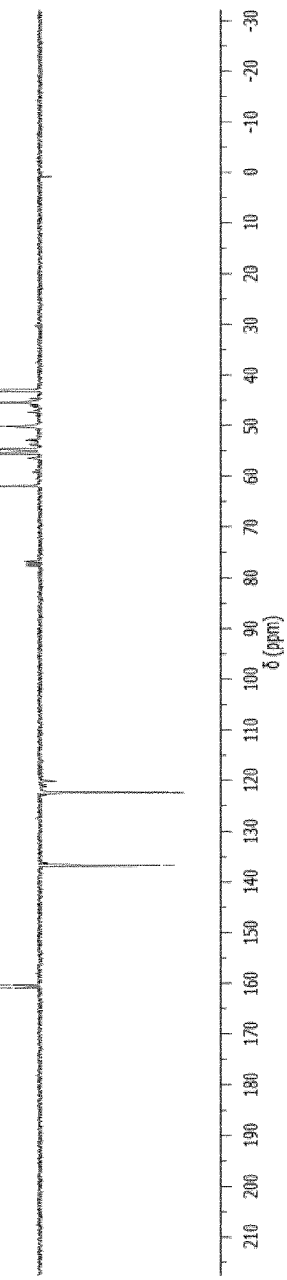
FIG. 5: $^{13}$C NMR spectrum of the compound 4 (CDCl$_3$, 75.45 MHz, 298K).

The examples below are given by way of illustration and are not limiting with respect to the present invention.

EXAMPLES

The acronyms used in the text below will have the following meanings:
ACN: acetonitrile
DCM: dichloromethane
DIPEA: diisopropylethylamine
EtOH: ethanol
MeOH: methanol
NaOH: sodium hydroxide
AT: ambient temperature
TFA: trifluoroacetic add
THF: tetrahydrofuran Example 1: Preparation of the Reinforced Ligands of Formula (I) According to the Invention 1—Condensing Step A According to the Invention:

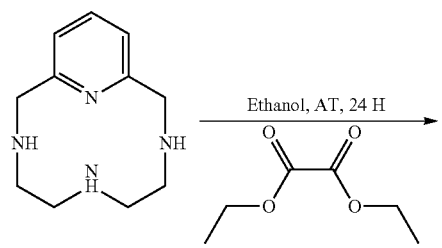

-continued

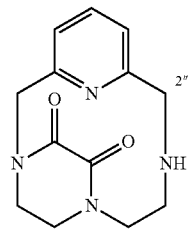

A solution of diethyl oxalate (2.02 g, 13.8 mmol) in EtOH (100 ml) was added to a solution of pyclen 1" (2.37 g, 11.5 mmol) in EtOH (200 ml). The mixture was stirred at ambient temperature overnight and then concentrated. The residue obtained was purified by alumina column chromatography (CH$_2$Cl$_2$/MeOH 98/2). The final product 2" was obtained in the form of a white solid (0.548 g, 19%) and corresponds to a compound of formula (XII) according to the invention.

$^1$H NMR (300 MHz, CDCl$_3$): δ 7.52 (t, 1H, $^3$J=7.7 Hz), 7.02 (d, 1H, $^3$J=7.9 Hz), 6.93 (d, 1H, $^3$J=7.5 Hz), 5.59 (d, 1H, $^2$J=16.2 Hz), 4.62 (ddd, 1H, $^2$J=13.9 Hz, $^3$J=11.1 Hz, $^3$J=2.5 Hz), 4.08 (d, 1H, $^2$J=16.6 Hz), 3.95 (d, 1H, $^2$J=17.3 Hz), 3.77 (ddd, 1H, $^2$J=13.9 Hz, $^3$J=10.6 Hz, $^3$J=4.52 Hz), 3.70 (d, 1H, $^2$J=17.3 Hz), 3.5 (ddd, 1H, $^2$J=12.4 Hz, $^3$J=10.6 Hz, $^3$J=4.5 Hz), 3.24 (dt, 1H, $^2$J=13.9 Hz, $^3$J=4.4 Hz), 3.13 (dt, 1H, $^2$J=12.4 Hz, $^3$J=4.1 Hz), 3.01 (dt, 1H, $^2$J=12.2 Hz, $^3$J=3.2 Hz), 2.83 (dt, 1H, $^2$J=13.9 Hz, $^3$J=3.0 Hz), 2.74 (td, 1H, $^2$J=11.7 Hz, $^3$J=2.3 Hz).

$^{13}$C NMR (75.47 MHz, CDCl$_3$): δ 162.96, 161.23, 159.10, 153.42, 136.83, 120.58, 119.44, 55.40, 52.53, 47.89, 47.66, 44.61, 44.20

Other Embodiment

A solution of diethyl oxalate (4.21 g, 28.49 mmol) in MeOH (100 ml) was added to a solution of pyclen 1" (5.88 g, 28.49 mmol) in MeOH (200 ml). The mixture was stirred at ambient temperature overnight and then concentrated. The residue obtained was taken up in dichloromethane, then the solution was filtered and concentrated in order to remove the unreacted pyclen 1". The solid was solubilized in methanol (5 ml) then ethyl acetate was added (150 ml). The crystals formed were filtered off and dried under vacuum. The final product 2" was obtained in the form of white crystals (6.28 g, 85%) and corresponds to a compound of formula (XII) according to the invention.

2—Following Steps According to the Invention:

The synthesis of compounds of formula (I) is carried out according to the following scheme:

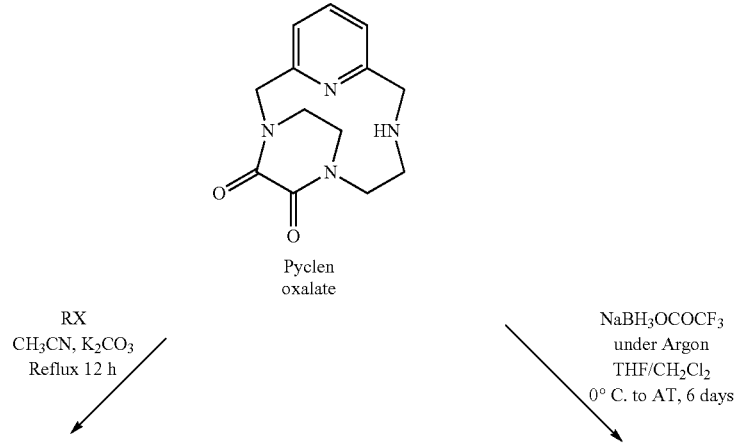

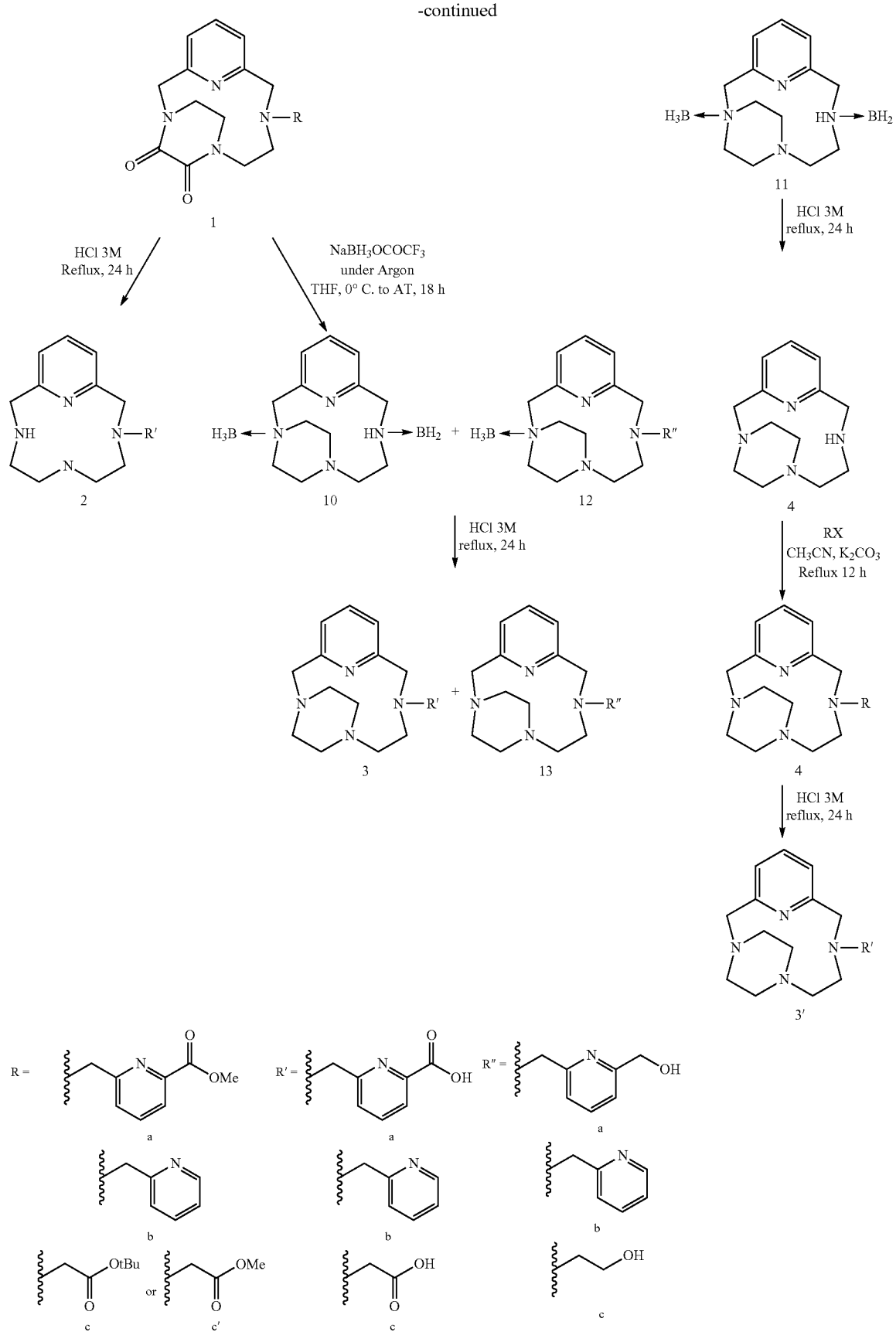

Compound 1a—Functionalizing Step B

The methyl ester of 6-chloromethylpyridine-2-carboxylic acid (711 mg, 3.85 mmol) is added to a solution of pyclen oxalate (1.0 g, 3.85 mmol) in acetonitrile (300 ml) in the presence of $K_2CO_3$ (1.5 g, 12 mmol). The reaction mixture is brought to reflux for four days, and is then filtered. The filtrate is concentrated, then is purified by column chromatography using neutral alumina as support (eluent: $CH_2Cl_2$/MeOH 98/2). After evaporation, the product 1a obtained is a yellow oil (1.56 g, 99%).

$^1$H NMR (300 MHz, $CDCl_3$): δ 7.90-7.80 (m, 2H), 7.72 (t, 1H, $^3J$=7.91 Hz), 7.38 (t, 1H, $^3J$=7.72 Hz), 6.97 (d, 1H, $^3J$=7.91 Hz), 6.65 (d, 1H, $^3J$=7.54 Hz), 5.59 (d, 1H, $^2J$=16.20 Hz), 4.70 (m, 1H), 4.19 (d, 1H, $^2J$=14.3 Hz), 4.12, 3.92 (m, 2H), 3.93 (s, 3H), 3.86 (d, 1H, $^2J$=14.3 Hz), 3.77-3.54 (m, 3H), 3.20 (m, 1H), 2.99-2.78 (m, 3H), 2.72 (m, 1H).

$^{13}$C NMR (75.47 MHz, $CDCl_3$): δ 165.71, 163.43, 160.97, 159.82, 158.63, 154.21, 146.15, 137.69, 136.67, 127.42, 123.44, 120.45, 119.28, 59.90, 59.47, 56.75, 53.02, 52.51, 46.19, 44.97, 44.68.

ESI-MS ($CH_3CN/H_2O$, 50/50): m/z 410.15 $[M+H]^+$, 432.10 $[M+Na]^+$.

Compound 1c—Functionalizing Step B

A solution of tert-butyl bromoacetate (0.668 g, 3.42 mmol) in acetonitrile (100 ml) is added to a solution composed of pyclen oxalate (0.890 g, 3.42 mmol) and of $K_2CO_3$ (1.42 g, 10.3 mmol) in acetonitrile (150 ml). The reaction medium is stirred at ambient temperature for 24 h. The solvent is evaporated off and then the residue obtained is taken up in dichloromethane. The product is then filtered and then concentrated. The product 1c obtained is a yellow oil that will be used in the following step without additional purification (1.25 g).

$^1$H NMR (300 MHz, $CDCl_3$): δ 7.28 (t, 1H, $^3J$=7.7 Hz), 6.8 (d, 1H, $^3J$=7.5 Hz), 6.63 (d, 1H, $^3J$=7.5 Hz), 5.26 (d, 1H, $^2J$=16.6 Hz), 4.08 (m, 1H), 3.89 (d, 1H, $^2J$=16.6 Hz), 3.68 (m, 4H), 3.0 (m, 4H), 2.77 (m, 2H), 2.52 (m, 1H), 1.18 (m, 9H).

$^{13}$C NMR (75.47 MHz, $CDCl_3$): δ 170.65, 162.42, 159.73, 158.43, 153.60, 136.48, 119.67, 119.11, 80.37, 61.08, 56.45, 52.59, 52.07, 46.64, 46.07, 44.76, 27.61.

ESI-HR-MS (positive, $H_2O$) m/z calculated for $[C_{19}H_{27}N_4O_4]^+$, 375.2027; obtained 375.2027 $[M+H]^+$, calculated for $[C_{19}H_{26}N_4O_4Na]^+$, 397.1846; obtained 397.1846 $[M+Na]^+$, calculated for $[C_{15}H_{19}N_4O_4]^+$, 319.1400; obtained 319.1400 $[M-tBu+2H]^+$.

Compound 1c"—Functionalizing Step B

A solution of methyl bromoacetate (587 mg; 3.38 mmol) in acetonitrile (13 ml) is added to a solution composed of pyclen oxalate (1.0017 g; 3.38 mmol) and of $K_2CO_3$ (796 mg; 5.76 mmol) in acetonitrile (13 ml). The reaction medium is stirred at ambient temperature for 4 h. After evaporation, the foam obtained is taken up in ethyl acetate (100 ml) and washed with the minimum amount of water (3 ml). The organic phase is dried over $MgSO_4$, filtered and evaporated to give the product 1c' in the form of a white foam (1.093 g; 97%)

$^1$H NMR (300 MHz, $CDCl_3$): δ 7.48 (t, J=7.6 Hz, 1H), 7.00 (d, J=7.6 Hz, 1H), 6.83 (d, J=7.5 Hz, 1H), 5.55 (d, J=16.5 Hz, 1H), 4.46-4.27 (m, 1H), 4.14-3.80 (m, 4H), 3.62 (s, 3H), 3.45 (d, J=18.0 Hz, 1H), 3.34-3.20 (m, 2H), 3.15 (d, J=11.9 Hz, 1H), 2.96 (d, J=10.2 Hz, 2H), 2.77-2.56 (m, 1H).

$^{13}$C NMR (75.47 MHz, $CDCl_3$): δ 172.33, 162.83, 160.22, 158.84, 154.07, 136.87, 120.11, 119.48, 61.46, 57.08, 52.34, 52.13, 51.19, 46.82, 46.38, 45.33

Compound 2a—Obtaining a Nonreinforced Pyclen not Belonging to the Invention

Hydrochloric acid (20 ml, 3 M) is added to the compound 1a (0.200 g, 0.49 mmol). The reaction medium is brought to reflux for 24 h and is then concentrated. The desired compound 2a is a colored oil (190 mg, 86% calculated for the hydrochloride salt).

$^1$H NMR (300 MHz, $D_2O$): δ 8.19 (t, 1H), 8.01 (d, 1H), 7.88 (d, 1H), 7.61 (t, 1H), 7.23 (d, 1H), 6.95 (d, 1H), 4.54 (s, 2H), 4.52 (s, 2H), 4.18 (s, 2H), 3.57 (m, 2H), 3.42-3.30 (m, 6H).

$^{13}$C NMR (75.47 MHz, $D_2O$): δ 166.48, 163.95, 157.07, 154.55, 153.60, 147.50, 146.03, 142.48, 132.14, 128.92, 125.91, 125.67, 61.36, 60.27, 54.61, 52.09, 46.73, 45.76.

ESI-HR-MS (positive, $H_2O$) m/z calculated for $[C_{18}H_{24}N_5O_2]^+$ 342.192451, obtained: 342.192738 $[M+H]^+$; calculated for $[C_{18}H_{23}N_5NaO_2]^+$ 364.174396, obtained: 384.174089 $[M+Na]^+$; calculated for $[C_{18}H_{23}N_5O_2]^{2+}$: 162.594582, obtained: 162.594105 $[M+2H—H_2O]^{2+}$; calculated for $[C_{18}H_{25}N_5O_2]^{2+}$ 171.599864, obtained: 171.599371 $[M+2H]^{2+}$ Compound 2c—Obtaining a Nonreinforced Pyclen not Belonging to the Invention The compound 1c' (338.9 mg, 1.01 mmol) is solubilized in ultrapure hydrochloric acid (10 ml, 3 M). The reaction mixture is heated at 70'C for 2.5 days and is then evaporated. The brown oil is taken up in the minimum amount of HCl and the product is precipitated with acetone (20 ml). The precipitate is analyzed on C-18 HPLC ($H_2O$ 0.1% TFA/ACN 0.1% TFA; 98/2>10/90) to give a separatable mixture of the expected product 2c and of the corresponding lactam.

Figure 6:
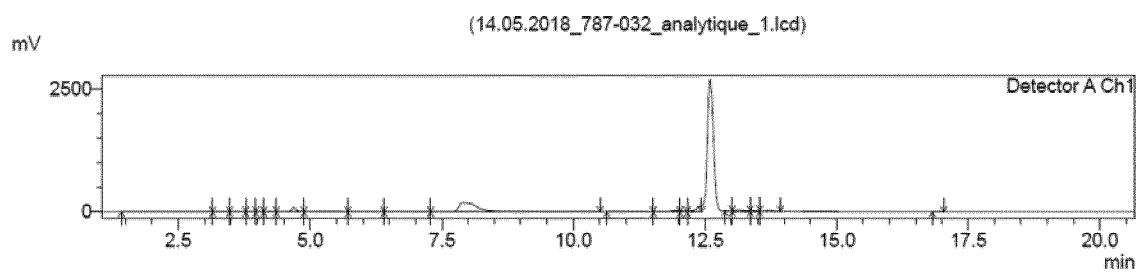
FIG. 6: Spectrum obtained by HPLC-MS during the analysis of the precipitate containing the compound 2c and the corresponding lactam.

FIG. 6 provides the spectrum obtained by HPLC-MS.

$T_R$=8 min: m/z: calculated for $[C_{13}H_{19}N_4O]^+$: 247.15, obtained: 247.20 $[M+H]^+$ $T_R$=12.5 min: m/z: calculated for $[C_{13}H_{21}N_4O_2]^+$: 265.16, obtained: 265.20 $[M+H]^+$ Compound 10a—Reducing Step C Under an inert atmosphere, a solution of trifluoroacetic acid (1.984 g, 17.4 mmol) in anhydrous THF (5 ml) is slowly added to a suspension of $NaBH_4$ (693 mg, 18.3 mmol) in anhydrous THF (5 ml) cooled to 0° C. The reaction mixture is stirred at the same temperature for 5 minutes. The compound 1a (452.8 mg, 1.11 mmol) solubilized in a THF/DCM 1:1 mixture (10 ml) is then slowly added to the reaction medium. The mixture is stirred at the same temperature for 10 min, then overnight at ambient temperature. Water and 10 M sodium hydroxide are added in order to neutralize the excess $NaBH_3OCOCF_3$. The borane is then extracted with DCM (3×20 ml), and the combined organic phases are dried over $MgSO_4$, filtered on a frit and evaporated off. The compound 10a is thus obtained without additional purification (white foam; 227.5 mg; 54%)

$^{13}$C NMR (75.47 MHz, $D_2O$): δ 165.34, 159.02, 158.67, 153.76, 147.27, 138.50, 137.81, 125.61, 124.54, 124.36, 123.73, 69.58, 67.54, 60.53, 60.19, 60.06, 55.30, 47.66

ESI-MS ($CH_3CN/H_2O$, 50/50): m/z calculated for $[C_{21}H_{28}N_5O_2]^+$ 382.22, obtained 382.15 $[M+H-2BH_3]^+$ Compound 10c—Reducing Step C In a 50 ml round-bottomed flask, under argon, a solution of trifluoroacetic acid (1.559 g; 13.68 mmol) in anhydrous THF (6 ml) is added dropwise to a suspension of $NaBH_4$ (545.3 mg; 14.4 mmol) in anhydrous THF (6 ml) cooled to 0° C. The reaction mixture is stirred at the same temperature for 5 min, then a solution of the compound 1c' (321.2 mg; 0.96 mmol) in dichloromethane (4 ml) is added dropwise to the reducing agent at 0'C. The reaction mixture is stirred for 10 min at the same temperature, then at 30° C. overnight. After 18 hours, the precipitate is filtered off on a frit of porosity 4, then a solution of NaOH (10 M; 4 ml) is added to the filtrate, as are ultrapure H$_2$O (15 ml) and DCM (20 ml). The desired product is then extracted with DCM (3×20 ml), and the combined organic phases are dried over MgSO$_4$, filtered on a frit and evaporated off. The compound 10c is thus obtained without additional purification (white foam; 250.4 mg; 82%)

$^{13}$C NMR (75.47 MHz, CDCl$_3$): δ 170.94, 158.77, 153.42, 138.41, 124.45, 124.21, 69.33, 67.44, 60.07, 59.04, 53.57, 51.16, 45.09.

ESI-MS (CH$_3$CN/H$_2$O, 50/50): m/z calculated for [C$_{16}$H$_{25}$N$_4$O$_2$]$^+$ 305.19, obtained 305.15

Compounds 3a and 13a—Hydrolysis Step

Compound 10a (204.9 mg; 0.53 mmol) is solubilized in ultrapure HCl (3M; 2.6 ml). The reaction mixture is stirred at 40° C. for 4 days, then at reflux for 2 days. The water is evaporated off. An oil is obtained. This oil is then purified by C18-HPLC chromatography (H$_2$O 0.1% HCl/acetonitrile: 90/10 to 5/95). The product 3a is then obtained in the form of a beige oil (45 mg, 20% calculated for the trifluoroacetate salt).

$^1$H NMR (500 MHz, D$_2$O): δ 8.56-8.53 (t, 1H), 8.29-8.28 (d, 1H), 8.13-8.11 (d, 1H), 7.96-7.93 (t, 1H), 7.60-7.58 (d, 1H), 7.45-7.44 (d, 1H), 4.92 (s, 2H), 4.79 (s, 2H), 4.57 (s, 2H), 4.15 (s, 2H), 3.87-3.84 (m, 4H), 3.40 (br s, 4H), 3.20-3.18 (t, 2H)

$^{13}$C NMR (125 MHz, D$_2$O): δ 166.68, 160.01, 156.08, 152.05, 149.33, 148.24, 143.26, 130.80, 129.02, 128.23, 128.13, 63.22, 61.62, 59.12, 56.66, 51.68, 46.08

ESI-HR-MS (positive, H$_2$O): m/z calculated for [C$_{20}$H$_{26}$N$_5$O$_2$]$^{2+}$ 368.2081, obtained 368.2078; [M+H]$^+$, calculated for [C$_{20}$H$_{26}$N$_5$O$_2$]$^{2+}$ 184.6076, obtained 184.6078 [M+2H]$^{2+}$.

Analytical C-18 HPLC (H$_2$O 0.1% TFA/ACN 0.1% TFA 98/2>20/80): t$_R$: 18.42 min m/z calculated for [C$_{20}$H$_{26}$N$_5$O$_2$]$^+$ 368.21; obtained 368.25 [M+H]$^+$; purity: 91%

During the purification of the compound 3a, the compound 13a is also obtained in the form of a beige oil (9.8 mg).

$^1$H NMR (500 MHz, D$_2$O): δ 8.51 (t, J=8.0 Hz, 1H), 8.05 (d, J=7.9 Hz, 1H), 7.98 (t, J=7.8 Hz, 1H), 7.90 (d, J=8.0 Hz, 1H), 7.60 (d, J=7.6 Hz, 1H), 7.49 (d, J=7.9 Hz, 1H), 5.03 (s, 2H), 4.90 (s, 2H), 4.46 (s, 2H), 4.07 (s, 2H), 3.91-3.74 (m, 4H), 3.44 (s, 4H), 3.10 (t, J=4.7 Hz, 2H).

$^{13}$C NMR (125 MHz, D$_2$O): δ 161.14, 158.42, 155.42, 151.94, 149.29, 143.29, 128.99, 128.56, 127.54, 126.15, 63.51, 62.32, 61.60, 57.74, 56.68, 50.65

ESI-HR-MS (positive, H$_2$O): m/z calculated for [C$_{20}$H$_{28}$N$_5$O]$^+$ 354.228837, obtained 354.228823 [M+H]$^+$; calculated for [C$_{20}$H$_{29}$N$_5$O]$^{2+}$ 177.618057, obtained 177.618215 [M+2H]$^{2+}$; calculated for [C$_{13}$H$_{19}$N$_4$]$^+$ 231.160423, obtained 231.160338 [M-fragmentation]$^+$; calculated for [C$_{20}$H$_{27}$N$_5$]$^{2+}$ 168.612774, obtained 168.612527 [M+2H—H$_2$O]$^{2+}$; calculated for [C$_7$H$_8$N]$^+$ 106.065126, obtained 106.065011 [fragment]$^+$.

Compound 3c—Hydrolysis Step

The compound 10c (250.4 mg; 0.78 mmol) is solubilized in ultrapure HCl (3M; 4.8 ml). The reaction mixture s stirred at reflux for 20 h. After evaporation, an orange oil is obtained. This oil is then purified by C18-HPLC chromatography (H$_2$O 0.1% TFA/acetonitrile 0.1% TFA: 98/2>20/ 80); the product 3c is then obtained in the form of a beige oil (97.9 mg, 25% calculated for the trifluoroacetate salt).

$^1$H NMR (500 MHz, D$_2$O): δ 7.95-7.92 (t, 1H), 7.52-7.47 (2d, 2H), 4.80 (s, 2H), 4.28 (s, 2H), 3.89-3.84 (m, 6H), 3.57 (br s, 2H), 3.35 (m, 2H), 3.26-3.25 (m, 2H), 3.12-3.10 (m, 2H)

$^{13}$C NMR (125 MHz, D$_2$O): δ 177.08, 160.30, 151.45, 143.16, 129.30, 127.70, 63.06, 62.91, 62.81, 58.04, 57.92, 57.25, 52.15, 49.98, 46.49.

ESI-HR-MS (positive, H$_2$O): m/z calculated for [C$_{15}$H$_{23}$N$_4$O$_2$]$^+$ 291.181552, obtained 291.181585 [M+H]$^+$; calculated for [C$_{15}$H$_{24}$N$_4$O$_2$]$^{2+}$ 146.094414, obtained 146.094221 [M+2H]$^{2+}$.

Analytical C-18 HPLC (H$_2$O 0.1% TFA/ACN 0.1% TFA 98/2>20/80): t$_R$: 16.57 min m/z calculated for [C$_{15}$H$_{23}$N$_4$O$_2$]$^+$ 291.18; obtained 291.25 [M+H]$^+$; purity: 98%

Compound 11—Reducing Step C

Under an inert atmosphere, a solution of trifluoroacetic acid (6.2713 g, 55 mmol) in anhydrous THF (10 ml) is slowly added to a suspension of NaBH (2.196 g, 58 mmol) in anhydrous THF (30 ml) cooled to 0° C. The pyclen oxalate (1 g, 3.84 mmol) solubilized in an anhydrous CH$_2$Cl$_2$/MeOH mixture (10 ml/50 μL) is then slowly added to the reaction medium, at 0° C. with vigorous stirring. The mixture is stirred at 0° C. for 30 min, then for two days at ambient temperature.

The reaction medium is then filtered on sintered glass of porosity 4, and a solution of NaOH (10 M; 10 ml) is added to the filtrate. After vigorous stirring of the two-phase mixture for 5 min at AT, 40 ml of ultrapure water and 100 ml of DCM are added; the desired product is extracted in the organic phase with 3×100 ml of DCM. The organic phases are combined, dried over MgSO$_4$, filtered and evaporated off to give the crude product (white foam; 875.6 mg).

The crude product (642.3 mg) is purified on a short column of basic alumina (Ø3 cm; ‡ 5 cm) with a DCM/ MeOH gradient (100/0→85/15) so as to give the compound 11 in boron salt form (white crystals; 208.7 mg; 21% (calculated for 2 BH$_3$)).

Figure 7:
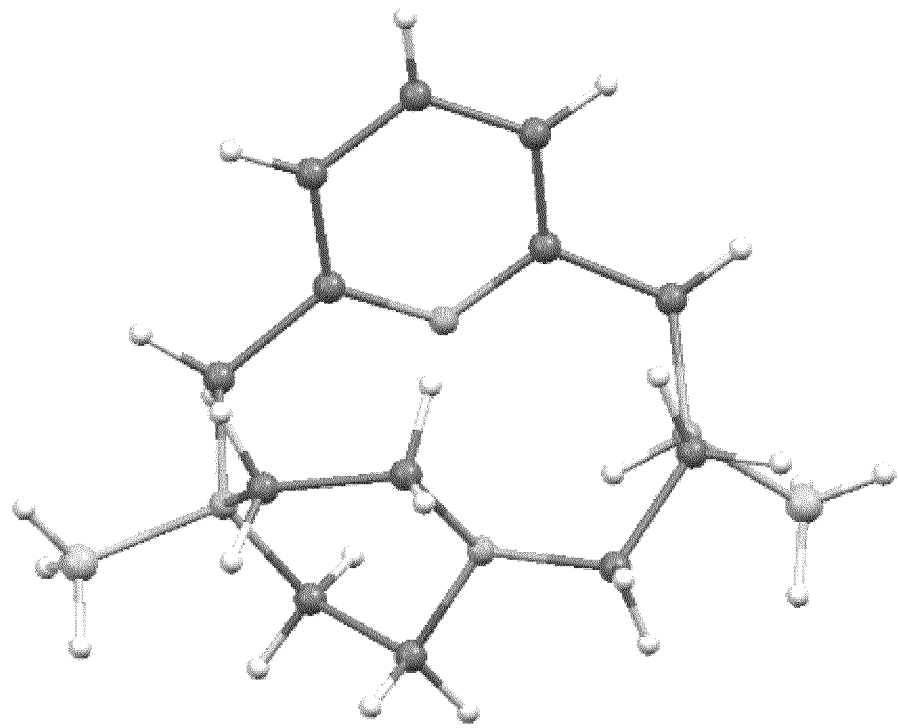
FIG. 7: Structure of the compound 11 obtained by X-ray diffraction.

FIG. 7 gives the structure obtained by X-ray diffraction of the compound 11, and proves that its formula is the following:

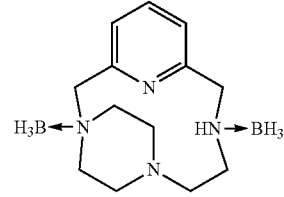

ESI-HR-MS (positive, H$_2$O): m/z calculated for [C$_{13}$H$_{21}$N$_4$]$^+$: 233.176073 m/z; found: 233.175875 [M+H]$^+$ $^1$H NMR (500 MHz, CDCl$_3$): δ 7.72 (t, J=7.7 Hz, 1H), 7.27 (2d, J=7.0, 3.1 Hz, 2H), 5.71 (s, 1H), 4.49 (td, J=11.4, 4.7 Hz, 1H), 4.35 (dd, J=14.5, 8.4 Hz, 2H), 4.20 (d, J=14.5 Hz, 1H), 3.69 (dd, J=14.5, 10.4 Hz, 2H), 3.55-3.41 (m, 1H), 3.41-3.30 (m, 1H), 3.22-3.10 (m, 1H), 2.82 (dd, J=14.7, 6.7 Hz, 2H), 2.61 (dd, J=14.8, 5.3 Hz, 1H), 2.47 (d, J=14.2 Hz, 1H), 2.25 (td, J=12.4, 2.6 Hz, 1H), 2.03 (dd, J=19.4, 11.1 Hz, 2H), 0.86 (td, J=11.3, 7.3 Hz, 1H).

$^1$H NMR (125 MHz, CDCl$_3$): δ 154.56, 153.19, 138.09, 125.13, 123.95, 69.37, 62.67, 62.48, 61.14, 60.79, 60.52, 53.55, 52.23, 50.78, 47.04, 44.76.

Compound 4—Hydrolysis Step

A solution of ultrapure hydrochloric acid (3M, 2.2 ml) is added to the compound 11 in order to hydrolyze the aminoborane bonds. The acid mixture obtained is brought to 40'C for 3 days. NaOH pellets are added in order to adjust the pH to 12-14. The aqueous phase is extracted with dichloromethane (3×25 ml) and the organic phase is dried over $MgSO_4$, filtered and concentrated. The compound 4 obtained is a yellow solid (90 mg, 100%).

$^1$H NMR (500 MHz, $CDCl_3$): δ 7.57 (t, J=7.6 Hz, 1H), 7.10 (dd, J=7.3, 5.3 Hz, 2H), 4.19 (s, 2H), 3.97 (s, 2H), 3.35-3.25 (m, 2H), 3.07 (d, J=10.7 Hz, 2H), 2.87 (d, J=4.4 Hz, 2H), 2.73 (d, J=2.6 Hz, 2H), 2.37 (s, 2H).

$^{13}$C NMR (125 MHz, $CDCl_3$): δ 160.98, 160.00, 137.12, 122.42, 122.31, 61.97, 55.80, 54.57, 49.61, 45.87, 43.15.

Example 2: Preparation of Complexes According to the Invention

Preparation of the [Mn(2a)]($ClO_4$) Complex

The compound 3a.3HCl (20 mg, 0.044 mmol) is dissolved in water (5 ml) and the pH of the solution is adjusted to 5 with a 1M KOH solution. A solution of $Mn(ClO_4)_2.6H_2O$ (16 mg, 0.044 mmol) in water (2 ml) is added to the ligand solution. The reaction medium is brought to reflux for 1 h and is then concentrated.

Figure 8:
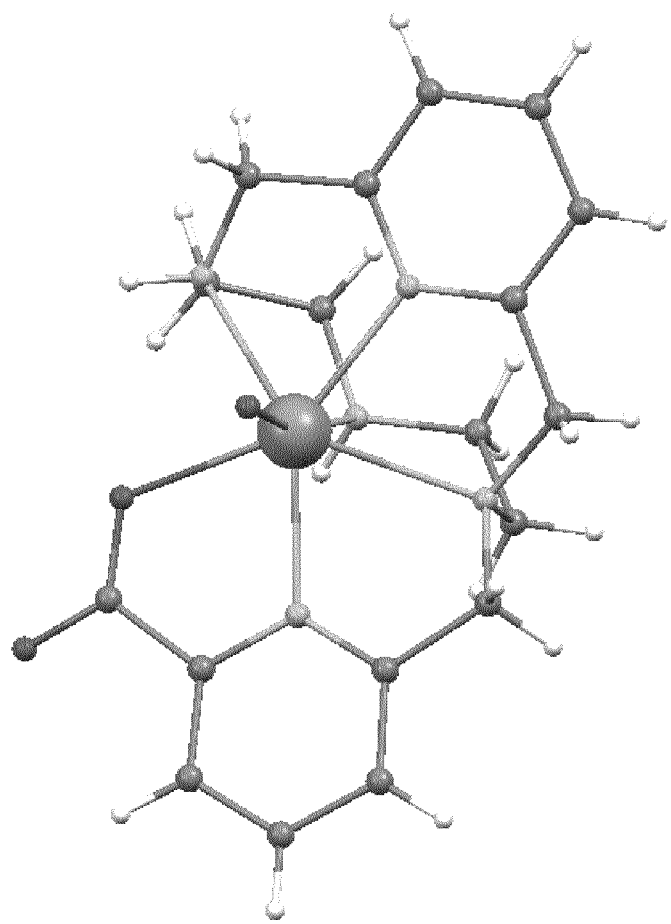
FIG. 8: Structure of the [Mn(2a)](ClO$_4$) complex obtained by X-ray diffraction.

FIG. 8 gives the structure obtained by X-ray diffraction of the [Mn(2a)]($ClO_4$) complex. ESI-HR-MS (positive, $H_2O$): m/z calculated for $[C_{18}H_{22}MnN_5O_2]^+$ 395.114846, obtained 395.114156; calculated for $[C_{18}H_{23}MnN_5O_2]^{2+}$ 198.061061, obtained 198.061026.

Preparation of the [Zn(2a)]($ClO_4$) Complex

The compound 3a.3HCl (20 mg, 0.044 mmol) is dissolved in water (5 ml) and the pH of the solution is adjusted to 5 with a 1M KOH solution. A solution of $Zn(ClO_4)_2.6H_2O$ (16.5 mg, 0.044 mmol) in water (2 ml) is added to the ligand solution. The reaction medium is brought to reflux for 1 h and is then concentrated.

ESI-HR-MS (positive, $H_2O$): m/z calculated for $[C_{18}H_{22}ZnN_5O]^+$ 404.105944, obtained 404.106289; calculated for $[C_{18}H_{23}ZnN_5O_2]^{2+}$ 202.556610, obtained 202.557059.

Preparation of the [Cu(2a)]($ClO_4$) Complex

The compound 3a.3HCl (20 mg, 0.044 mmol) is dissolved in water (5 ml) and the pH of the solution is adjusted to 5 with a 1M KOH solution. A solution of $Cu(ClO_4)_2.6H_2O$ (16.4 mg, 0.044 mmol) in water (2 ml) is added to the ligand solution. The reaction medium is brought to reflux for 1 h and is then concentrated.

ESI-HR-MS (positive, $H_2O$): m/z calculated for $[C_{18}H_{22}CuN_5O_2]^+$ 403.106399, obtained 403.106320; calculated for $[C_{18}H_{23}CuN_5O_2]^{2+}$ 202.056838, obtained 202.056983.

Preparation of the [Zn(3a)](Cl) Complex

In a G10 glass vessel, under an argon stream, a solution of $ZnCl_2$ (11.58 mg; 0.085 mmol) in anhydrous 1-butanol (1 ml) is added to a solution of the compound 3a (8.2 mg; 0.017 mmol) in the same solvent (1 ml) in the presence of DIPEA (5.9 μL; 0.034 mmol). The mixture is then stirred with microwaves at 130'C for 8 h. After returning to AT, all of the reaction medium is transferred into a 50 ml Falcon™ tube and centrifuged at 4000 g for 12 min. The supernatant is removed and the precipitate is rinsed with THF (2×5 ml) by centrifugation. The precipitate is solubilized in water and evaporated to give the expected complex in the form of a beige powder (4.5 mg; 57%).

Maldi-MS (ditranol, $HCCA/H_2O$ 1:1): for $C_{20}H_{24}N_5O_2Zn^+$ m/z obtained: 430.30, m/z calculated: 430.12 $[M]^+$; for $C_{20}H_{26}N_5O_3Zn^+$ m/z obtained: 448.30, m/z calculated: 448.13 $[M+H_2O]^+$ Preparation of the [Cu(3a)]($ClO_4$) Complex In a G10 glass vessel, under an argon stream, a solution of $Cu(ClO_4)_2.6H_2O$ (50 mg; 0.12 mmol) in anhydrous 1-butanol (1.3 ml) is added to a solution of the compound 3a (13.3 mg; 0.027 mmol) in the same solvent (1.4 ml) in the presence of DIPEA (9.4 μl; 0.054 mmol). The mixture is then stirred with microwaves at 130° C. for 8 h. After returning to AT, all of the reaction medium is transferred into a 50 ml Falcon™ tube and centrifuged at 4000 g for 12 min. The supernatant is removed and the precipitate is rinsed with THF (2×5 ml) by centrifugation. The precipitate is solubilized in water and slowly evaporated to give the expected complex in the form of blue needles (12.8 mg; 89%).

ESI-MS (positive, $H_2O$/ACN 50/50 0.1% TFA): for $C_{20}H_{24}N_5O_2Cu$ m/z obtained: 429.05, m/z calculated: 429.12 $[M]^+$; for $C_{20}H_{25}N_5O_2Cu^{2+}$ m/z obtained: 215.10, m/z calculated: 215.06 $[M+H]^{2+}$; for $C_{22}H_{25}F_3N_5O_4Cu^+$ UV: the UV analysis shows an absorbance characteristic of a d→d transition of the $Cu^{2+}$ of the complex at $\lambda_{max}$=650 nm with a molar absorption coefficient ε=103 $l·mol^{-1}·cm^{-1}$.

Preparation of the [Mn(3a)]($ClO_4$) Complex

In a G10 glass vessel, under an argon stream, a solution of $Mn(ClO_4)_2.6H_2O$ (44.4 mg; 0.175 mmol) in anhydrous 1-butanol (1.7 ml) is added to a solution of the compound 3a (14.6 mg; 0.035 mmol) in the same solvent (1.8 ml) in the presence of DIPEA (12.2 μl; 0.07 mmol). The mixture is stirred with microwaves at 130° C. for 8 h. After returning to AT, all of the reaction medium is transferred into a 50 ml Falcon™ and centrifuged at 4000 g for 12 min. The supernatant is removed and the precipitate is rinsed with THF (2×5 ml) by centrifugation. The precipitate is solubilized in water and evaporated to give the expected complex in the form of an orange powder (4.5 mg; 25%).

Maldi-MS (ditranol, $HCCA/H_2O$ 1:1): for $C_{20}H_{26}MnN_5O_3^+$ m/z obtained: 439.506, m/z calculated: 439.141 $[M+H_2O]^+$

The invention claimed is:
1. A compound of formula (I)

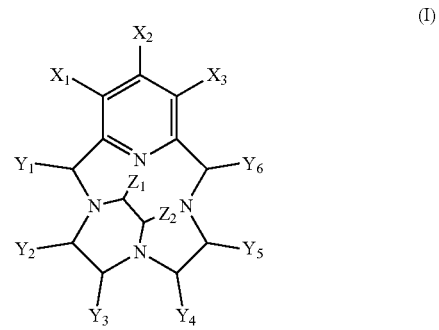

wherein:
$X_1$, $X_2$, $X_3$, $Y_1$, $Y_2$, $Y_3$, $Y_4$, $Y_5$ and $Y_6$ are independently selected from the group consisting of:
H, $(C_1-C_{20})$alkyl, $(C_2-C_{20})$alkenyl, $(C_2-C_{20})$alkynyl, $(C_6-C_{10})$aryl, halogen, azide (—$N_3$), —C(O)ORa, —ORa, —N(Ra)(Rb), —C(O)—N(Ra)(Rb), —SH, —SRa, —SO₂OH, —SO₂—N(Ra)(Rb), —SCN, and a functional chemical group which allows grafting to a vector or to a biomolecule wherein said functional chemical group is selected from the group consisting of succinimidyl, N-hydroxysuccinimidyl, sulfosuccinimidyl, maleimidyl, biotinyl, squarate, and

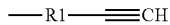

wherein R1 is an alkylene, thiol, azide, hydrazine and isothiocyanate, wherein Ra and Rb are independently either H or ($C_1$-$C_{20}$)alkyl group; and
  wherein:
    one or more of said alkyl, alkenyl, and alkynyl groups optionally comprises one or more heteroatoms, one or more ($C_6$-$C_{10}$)arylenes, and/or one or more biphenylene(s) in its/their chain(s); and
    one or more of said alkyl, alkenyl, alkynyl, and ($C_6$-$C_{20}$)aryl groups optionally is substituted with one or more substituent(s) selected from the group consisting of:
      halogen, —C(O)ORc, —ORc, —N(Rc)(Rd), —C(O)-N(Rc)(Rd), —SH, —SRc, —SO₂OH, —SO₂—N(Rc)(Rd) —SCN, ($C_6$-$C_{10}$)aryl, and a functional chemical group which allows grafting to a vector or a biomolecule wherein said functional chemical group is selected from the group consisting of succinimidyl, N-hydroxysuccinimidyl, sulfosuccinimidyl, maleimidyl, biotinyl, squarate, and

wherein R1 is an alkylene, thiol, azide, hydrazine and isothiocyanate;
  wherein Rc and Rd are independently either H or a ($C_1$-$C_{20}$)alkyl group, wherein said ($C_1$-$C_{20}$)alkyl group is optionally substituted with one or more substituent(s) selected from the group consisting of: halogen, —C(O)ORe, —ORe, —N(Re)(Rf), —C(O)—N(Re)(Rf), —SH, —SRe, —SO₂OH, —SO₂—N(Re)(Rf) —SCN, ($C_6$-$C_{10}$)aryl, and a functional chemical group which allows grafting to a vector or a biomolecule wherein said functional chemical group is selected from the group consisting of succinimidyl, N-hydroxysuccinimidyl, sulfosuccinimidyl, maleimidyl, biotinyl, squarate, and

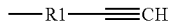

wherein R1 is an alkylene, thiol, azide, hydrazine and isothiocyanate; and
  wherein Re and Rf are independently either H or a ($C_1$-$C_{20}$)alkyl group;
$Z_1$ and $Z_2$ are independently selected from the group consisting of:
  H, ($C_1$-$C_4$)alkyl, halogen, —ORg, —N(Rg)(Rh), —SH, and —SRg;

wherein Rg and Rh are independently selected from the group consisting of:
  H, a ($C_1$-$C_4$)alkyl, 2-THP (tetrahydropyranyl), tosyl, nosyl or TMS (trimethylsilyl) group, —O—C(O)Rt, —C(O)Rt, —OC(O)ORt, —NH-C(O)—ORt, and —NH—C(O)Rt; and
wherein Rt is selected from the group consisting of: ($C_1$-$C_4$)alkyl, benzyl, allyl, and trifluoromethyl;
wherein one or more of said alkyl groups is optionally substituted with one or more substituent(s) selected from the group consisting of:
  halogen, —C(O)ORp, —ORp, —N(Rp)(Rq), —C(O)—N(Rp)(Rq), —SH, —SRp, —SO₂OH, —SO₂—N(Rp)(Rq), and —SCN;
wherein Rp and Rq are independently either H or a ($C_1$-$C_4$)alkyl group;
R is selected from the group consisting chosen from the group consisting of:
  H, ($C_1$-$C_{20}$)alkyl, ($C_2$-$C_{20}$)alkenyl, ($C_2$-$C_{20}$)alkynyl, ($C_1$-$C_{20}$)alkylene-W, ($C_2$-$C_{20}$)alkenylene-W, and ($C_2$-$C_{20}$)alkynylene-W;
wherein:
  one or more of said alkyl, alkenyl, alkynyl, alkylene, alkenylene, and alkynylene groups optionally comprise(s) one or more heteroatoms, one or more ($C_6$-$C_{10}$)arylenes, and/or one or more biphenylene(s) in its/their chain(s);
W is selected from the group consisting of:
  ($C_6$-$C_{10}$)aryl, heteroaryl consisting 5 to 10 atoms, biphenyl, —C(O)ORi, —C(O)—N(Ri)(Rj), —P(O)(ORi)(ORj), —(Rj)P(O)(ORi), —O—P(O)(ORi)(ORj), —SH, —SO₂OH, —SO₂—N(RO(Rj) and —SCN;
  wherein Ri and Rj are independently either H or a ($C_1$-$C_{20}$)alkyl group; and
  one or more of said alkyl, alkenyl, alkynyl, alkylene, alkenylene, alkynylene, aryl and heteroaryl groups is optionally be substituted with one or more substituent(s) selected from the group consisting of:
    ($C_1$-$C_{20}$)alkyl, ($C_2$-$C_{20}$)alkenyl, ($C_2$-$C_{20}$)alkynyl, halogen, —C(O)ORk, —ORk, —N(Rk)(Rl), —C(O)—N(Rk)(Rl), —SH, —SRk, —SO₂OH, —SO₂—N(Rk)(Rl), —SCN, ($C_6$-$C_{10}$)aryl and biphenyl;
  wherein Rk and Rl are independently either H or a ($C_1$-$C_{20}$)alkyl group, wherein said alkyl is optionally substituted with one or more substituents selected from the group consisting of:
    halogen, —C(O)ORm, —ORm, —N(Rm)(Rn), —C(O)—N(Rm)(Rn), —SH, —SRm, —SO₂OH, —SO₂—N(Rm)(Rn), —SCN, ($C_6$-$C_{10}$)aryl, and a functional chemical group which allows grafting to a vector or a biomolecule wherein said functional chemical group is selected from the group consisting of succinimidyl, N-hydroxysuccinimidyl, sulfosuccinimidyl, maleimidyl, biotinyl, squarate, and

wherein R1 is an alkylene, thiol, azide, hydrazine and isothiocyanate;
  wherein Rm and Rn are independently either H a ($C_1$-$C_{20}$)alkyl group; or a pharmaceutically acceptable salt of formula (I), an optical isomer of formula (I), a geometric isomer of formula (I), a tautomer of formula (I), or a solvate of formula (I).

2. The compound of claim 1, wherein:

R is selected from the group consisting of:
H, $(C_1-C_{20})$alkyl, $(C_1-C_{20})$alkylene-W;
wherein:
W is selected from the group consisting of:
$(C_6-C_{10})$aryl, heteroaryl consisting of 5 to 10 atoms, —C(O)ORi, —C(O)—N(Ri)(Rj), —P(O)(ORi)(ORj), —(Rj)P(O)(ORi), —O-P(O)(ORi)(ORj), —SH, —SO$_2$OH, —SO$_2$—N(RO(Rj) and —SCN;
wherein Ri and Rj are independently either H or a $(C_1-C_{20})$alkyl group; and
p one or more of said alkyl, alkylene, aryl and heteroaryl groups is optionally substituted with one or more substituent(s) chosen from the group consisting of:
$(C_1-C_{20})$alkyl, $(C_2-C_{20})$alkenyl, $(C_2-C_{20})$alkynyl, halogen, —C(O)ORk, ORk, —N(Rk)(Rl), —C(O)—N(Rk)(Rl), —SH, —SRk, —SO$_2$OH, —SO$_2$—N(Rk)(Rl), —SCN and $(C_6-C_{10})$aryl;
wherein Rk and Rl are independently either H or a $(C_1-C_{20})$alkyl group.

3. The compound of claim 1, wherein formula (I) corresponds to formula (II) set forth below

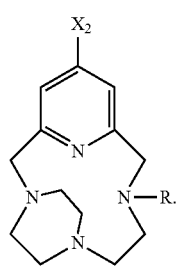

(II)

4. The compound of claim 3, wherein $X_2$ is H.

5. The compound of claim 1, wherein formula I corresponds to a structure selected from the group consisting of the following:

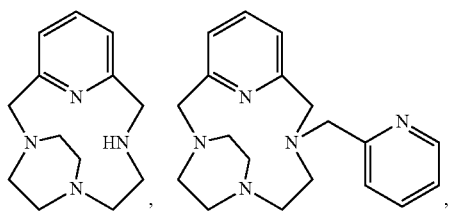

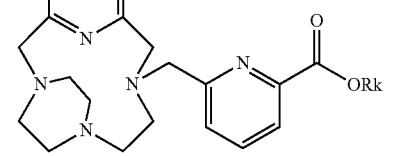

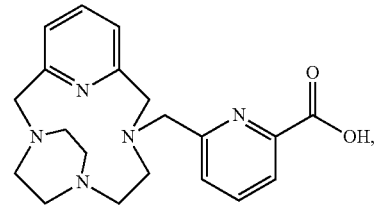

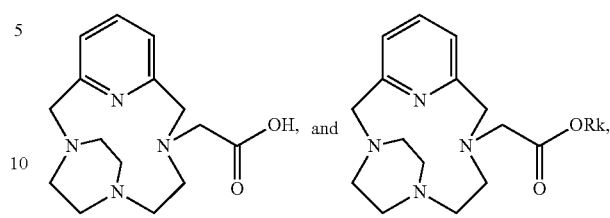

wherein Rk is H or a $(C_1-C_{20})$alkyl group.

6. The compound of claim 1, wherein formula I corresponds to a structure selected from the group consisting of the following:

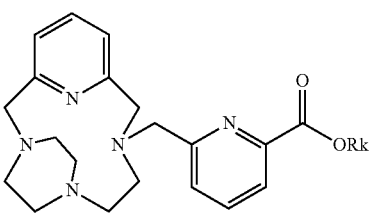

and

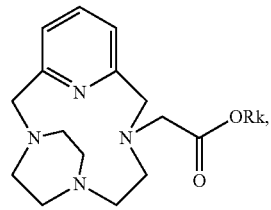

wherein Rk is H or a $(C_1-C_4)$alkyl group.

7. The compound of claim 1, wherein formula I corresponds to a structure selected from the group consisting of the following:

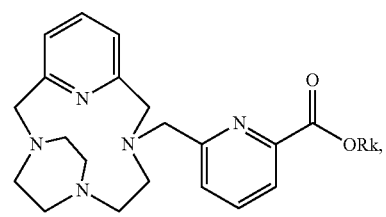

wherein Rk is t-butyl; and

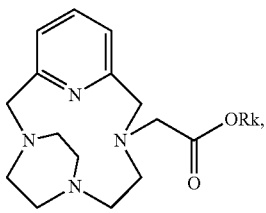

wherein Rk is a t-butyl.

8. A complex comprising a central atom M and the compound of claim 1.

9. The complex of claim 8, wherein M is a metal.

10. A method for treating a patient suffering from a cancer, the method comprising administering to said patent a therapeutic amount of the complex of claim 8.

11. A contrast product comprising the complex of claim 8.

12. A pharmaceutical composition comprising the compound of claim 1 and, optionally, one or more pharmaceutically acceptable excipient(s).

13. A pharmaceutical composition comprising the complex of claim 8 and, optionally, one or more pharmaceutically acceptable excipient(s).

14. A process for preparing the compound of claim 1, the process comprising reducing a compound of formula (XIII) below:

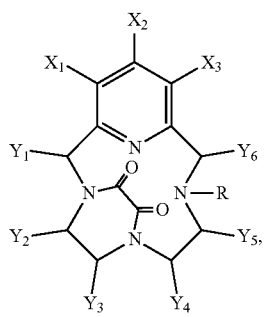

wherein $X_1$, $X_2$, $X_3$, $Y_1$, $Y_2$, $Y_3$, $Y_4$, $Y_5$, $Y_6$ and R are as defined for formula (I), in the presence of a mixture of a reducing agent $A\text{-}BH_4$ and of an organic acid, wherein A is selected from the group consisting of Li, Na, K, Zn and $(Me_3)N$, to obtain a compound of formula (I') below:

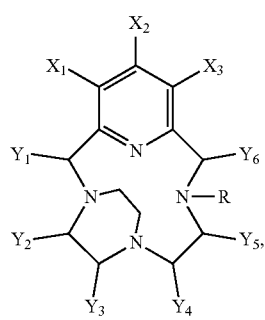

wherein $X_1$, $X_2$, $X_3$, $Y_1$, $Y_2$, $Y_3$, $Y_4$, $Y_5$, $Y_6$ and R are as defined for formula (I).

15. The process of claim 14, wherein A is Na and the organic acid is trifluoroacetic acid.

16. The process of claim 14 further comprising, before said reducing step, condensing a compound of formula (X) below:

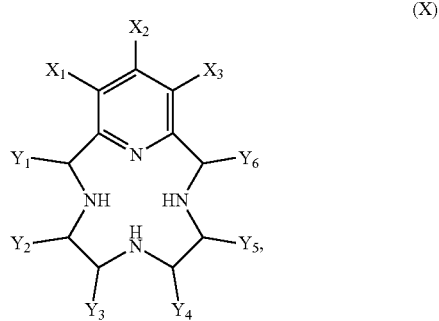

wherein $X_1$, $X_2$, $X_3$, $Y_1$, $Y_2$, $Y_3$, $Y_4$, $Y_5$ and $Y_6$ are as defined for formula (I), with a compound of formula (XI) below:

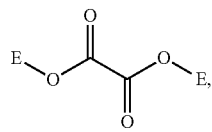

wherein is E a $(C_1\text{-}C_4)$alkyl, to obtain a compound of formula (XII) below:

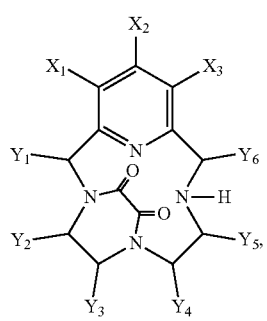

wherein $X_1$, $X_2$, $X_3$, $Y_1$, $Y_2$, $Y_3$, $Y_4$, $Y_5$ and $Y_6$ are as defined for formula (I).

17. The process of claim 16, wherein E is methyl or ethyl.

* * * * *